United States Patent
Woods et al.

(10) Patent No.: US 12,246,183 B1
(45) Date of Patent: *Mar. 11, 2025

(54) SELF-CENTERING POLYMERIC WASHER THAT PREVENTS MISALIGNMENT WHEN POSITIONED BETWEEN A FEEDTHROUGH AND A CIRCUIT BOARD SUPPORTING EMI FILTER CAPACITORS FOR A MEDICAL DEVICE

(71) Applicant: Greatbatch Ltd., Clarence, NY (US)

(72) Inventors: Jason Woods, Carson City, NV (US); Robert A. Stevenson, Canyon Country, CA (US); Christine A. Frysz, Orchard Park, NY (US); Thomas Marzano, East Amherst, NY (US); Keith W. Seitz, Clarence Center, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/631,709

(22) Filed: Apr. 10, 2024

Related U.S. Application Data

(63) Continuation-in-part of application No. 18/377,609, filed on Oct. 6, 2023, now Pat. No. 11,980,766.

(51) Int. Cl.
*A61N 1/375* (2006.01)
*F16B 43/00* (2006.01)
(Continued)

(52) U.S. Cl.
CPC .......... *A61N 1/3754* (2013.01); *F16B 43/001* (2013.01); *H01G 4/35* (2013.01);
(Continued)

(58) Field of Classification Search
CPC ..... A61N 1/3754; A61N 1/375; F16B 43/001; H01G 4/34; H01R 13/521; H01R 13/533;
(Continued)

(56) References Cited

U.S. PATENT DOCUMENTS

| | | |
|---|---|---|
| 3,137,808 A | 6/1964 | Coda et al. |
| 5,333,095 A | 7/1994 | Stevenson et al. |

(Continued)

FOREIGN PATENT DOCUMENTS

EP          3449973 A1      3/2019

*Primary Examiner* — Harshad C Patel
(74) *Attorney, Agent, or Firm* — Michael F. Scalise

(57) ABSTRACT

A self-centering washer is positioned between a feedthrough and a filter circuit board. The washer has openings through which first and second terminal pins extend. A first opening has an inner arcuate portion contacting the first terminal pin and an outer perimeter portion exposing the braze sealing the terminal pin to the insulator. A second opening has an inner arcuate portion contacting the second terminal pin and an outer perimeter portion exposing the braze sealing the terminal pin to the insulator. In an imaginary configuration with the first and second washer openings superimposed one on top of the other, the cumulative arcuate distance of the inner arcuate portions about one of the terminal pins, subtracting overlap, results in a gap between the superimposed washer openings that is less than a diameter of the first and second terminal pins so that the washer is prevented from lateral movement.

21 Claims, 18 Drawing Sheets

(51) Int. Cl.
*H01G 4/35* (2006.01)
*H01R 13/52* (2006.01)
*H01R 13/533* (2006.01)
*H05K 1/02* (2006.01)

(52) U.S. Cl.
CPC ......... *H01R 13/521* (2013.01); *H01R 13/533* (2013.01); *H05K 1/0218* (2013.01); *H05K 2201/10015* (2013.01)

(58) Field of Classification Search
CPC ...... H01R 13/52; H01R 13/46; H01R 13/523; H01R 13/53; H01R 13/5224; H05L 2201/10015
See application file for complete search history.

(56) References Cited

U.S. PATENT DOCUMENTS

| | | |
|---|---|---|
| 5,489,180 A | 2/1996 | Ichihara et al. |
| 5,751,539 A | 5/1998 | Stevenson et al. |
| 5,896,267 A | 4/1999 | Hittman et al. |
| 5,905,627 A | 5/1999 | Brendel et al. |
| 5,973,906 A | 10/1999 | Stevenson et al. |
| 5,978,204 A | 11/1999 | Stevenson |
| 6,008,980 A * | 12/1999 | Stevenson ................ H01G 4/35 361/309 |
| 6,529,103 B1 * | 3/2003 | Brendel ................... H01G 4/35 333/182 |
| 6,765,779 B2 | 7/2004 | Stevenson et al. |
| 6,765,780 B2 * | 7/2004 | Brendel ................ A61N 1/3754 361/306.1 |
| 6,882,248 B2 | 4/2005 | Stevenson et al. |
| 7,797,048 B2 * | 9/2010 | Stevenson ................ H01G 4/35 607/37 |
| 7,878,747 B2 | 2/2011 | Dean et al. |
| 7,957,806 B2 * | 6/2011 | Stevenson ............ A61N 1/3754 607/116 |
| 8,047,753 B2 | 11/2011 | Dean et al. |
| 8,095,224 B2 | 1/2012 | Truex et al. |
| 8,179,658 B2 * | 5/2012 | Brendel ................ A61N 1/3754 361/301.2 |
| 8,195,295 B2 | 6/2012 | Stevenson et al. |
| 8,196,295 B2 * | 6/2012 | Imafuku ............ H05K 13/0853 29/709 |
| 8,321,032 B2 | 11/2012 | Frysz et al. |
| 8,433,410 B2 | 4/2013 | Dabney et al. |
| 8,437,865 B2 | 5/2013 | Dabney et al. |
| 8,483,840 B2 | 7/2013 | Stevenson et al. |
| 8,604,341 B2 | 12/2013 | Barry et al. |
| 8,653,384 B2 | 2/2014 | Tang et al. |
| 8,670,841 B2 | 3/2014 | Dabney et al. |
| 8,712,544 B2 | 4/2014 | Dabney et al. |
| 8,761,895 B2 | 6/2014 | Stevenson et al. |
| 8,855,768 B1 | 10/2014 | Dabney et al. |
| 8,868,189 B2 | 10/2014 | Stevenson et al. |
| 8,918,189 B2 | 12/2014 | Dabney et al. |
| 8,927,862 B2 | 1/2015 | Barry et al. |
| 8,938,309 B2 | 1/2015 | Marzano et al. |
| 8,996,126 B2 | 3/2015 | Stevenson et al. |
| 9,014,808 B2 | 4/2015 | Dabney et al. |
| 9,031,670 B2 | 5/2015 | Dabney et al. |
| 9,064,640 B2 | 6/2015 | Brendel et al. |
| 9,071,221 B1 | 6/2015 | Stevenson et al. |
| 9,233,253 B2 | 1/2016 | Stevenson et al. |
| 9,352,150 B2 | 5/2016 | Stevenson et al. |
| 9,427,596 B2 | 8/2016 | Brendel et al. |
| 9,447,810 B2 | 9/2016 | Dean et al. |
| 9,463,329 B2 | 10/2016 | Frysz et al. |
| 9,492,659 B2 | 11/2016 | Brendel et al. |
| 9,511,220 B2 | 12/2016 | Marzano et al. |
| 9,521,744 B2 | 12/2016 | Barry et al. |
| 9,757,558 B2 | 9/2017 | Stevenson et al. |
| 9,764,129 B2 | 9/2017 | Stevenson et al. |
| 9,889,306 B2 | 2/2018 | Stevenson et al. |
| 9,895,534 B2 | 2/2018 | Stevenson et al. |
| 9,931,514 B2 | 4/2018 | Frysz et al. |
| 9,993,650 B2 | 6/2018 | Seitz et al. |
| 10,016,595 B2 | 7/2018 | Stevenson et al. |
| 10,016,596 B2 | 7/2018 | Stevenson et al. |
| 10,046,166 B2 | 8/2018 | Stevenson et al. |
| 10,080,889 B2 | 9/2018 | Marzano et al. |
| 10,092,749 B2 | 10/2018 | Stevenson et al. |
| 10,099,051 B2 | 10/2018 | Stevenson et al. |
| 10,124,164 B2 | 11/2018 | Stevenson et al. |
| 10,249,415 B2 | 4/2019 | Seitz et al. |
| 10,272,252 B2 | 4/2019 | Seitz et al. |
| 10,272,253 B2 | 4/2019 | Seitz et al. |
| 10,306,848 B2 | 6/2019 | Chan et al. |
| 10,350,421 B2 | 7/2019 | Stevenson et al. |
| 10,420,949 B2 | 9/2019 | Seitz et al. |
| 10,449,375 B2 | 10/2019 | Frustaci et al. |
| 10,499,375 B2 | 12/2019 | Jung et al. |
| 10,500,402 B2 * | 12/2019 | Stevenson ............ A61N 1/3754 |
| 10,559,409 B2 | 2/2020 | Seitz et al. |
| 10,561,837 B2 | 2/2020 | Stevenson et al. |
| 10,589,107 B2 | 3/2020 | Seitz et al. |
| 10,596,369 B2 | 3/2020 | Stevenson et al. |
| 10,722,706 B2 | 7/2020 | Stevenson et al. |
| 10,828,498 B2 | 11/2020 | Stevenson et al. |
| RE48,348 E | 12/2020 | Stevenson |
| 10,857,369 B2 | 12/2020 | Stevenson et al. |
| 10,874,866 B2 | 12/2020 | Stevenson et al. |
| 10,905,888 B2 | 2/2021 | Stevenson et al. |
| 10,912,945 B2 | 2/2021 | Stevenson et al. |
| 11,013,928 B2 | 5/2021 | Stevenson et al. |
| 11,071,858 B2 | 7/2021 | Stevenson et al. |
| 11,147,977 B2 | 10/2021 | Stevenson et al. |
| 11,185,705 B2 | 11/2021 | Stevenson et al. |
| 11,198,014 B2 | 12/2021 | Stevenson et al. |
| 11,211,741 B2 | 12/2021 | Marzano et al. |
| 11,241,581 B2 | 2/2022 | Stevenson et al. |
| 11,344,734 B2 * | 5/2022 | Stevenson .......... H01R 13/5224 |
| 11,406,817 B2 | 8/2022 | Stevenson et al. |
| 11,633,612 B2 | 4/2023 | Frysz et al. |
| 11,648,408 B2 | 5/2023 | Hussein |
| 11,764,745 B2 | 9/2023 | Sahabi et al. |
| 11,980,766 B2 * | 5/2024 | Woods ................ A61N 1/05 |
| 2003/0053284 A1 * | 3/2003 | Stevenson ................ H01G 4/35 361/302 |
| 2009/0080140 A1 * | 3/2009 | Iyer ................... B23K 35/0233 29/25.42 |
| 2022/0115806 A1 * | 4/2022 | Marzano ................ H01G 4/236 |

* cited by examiner

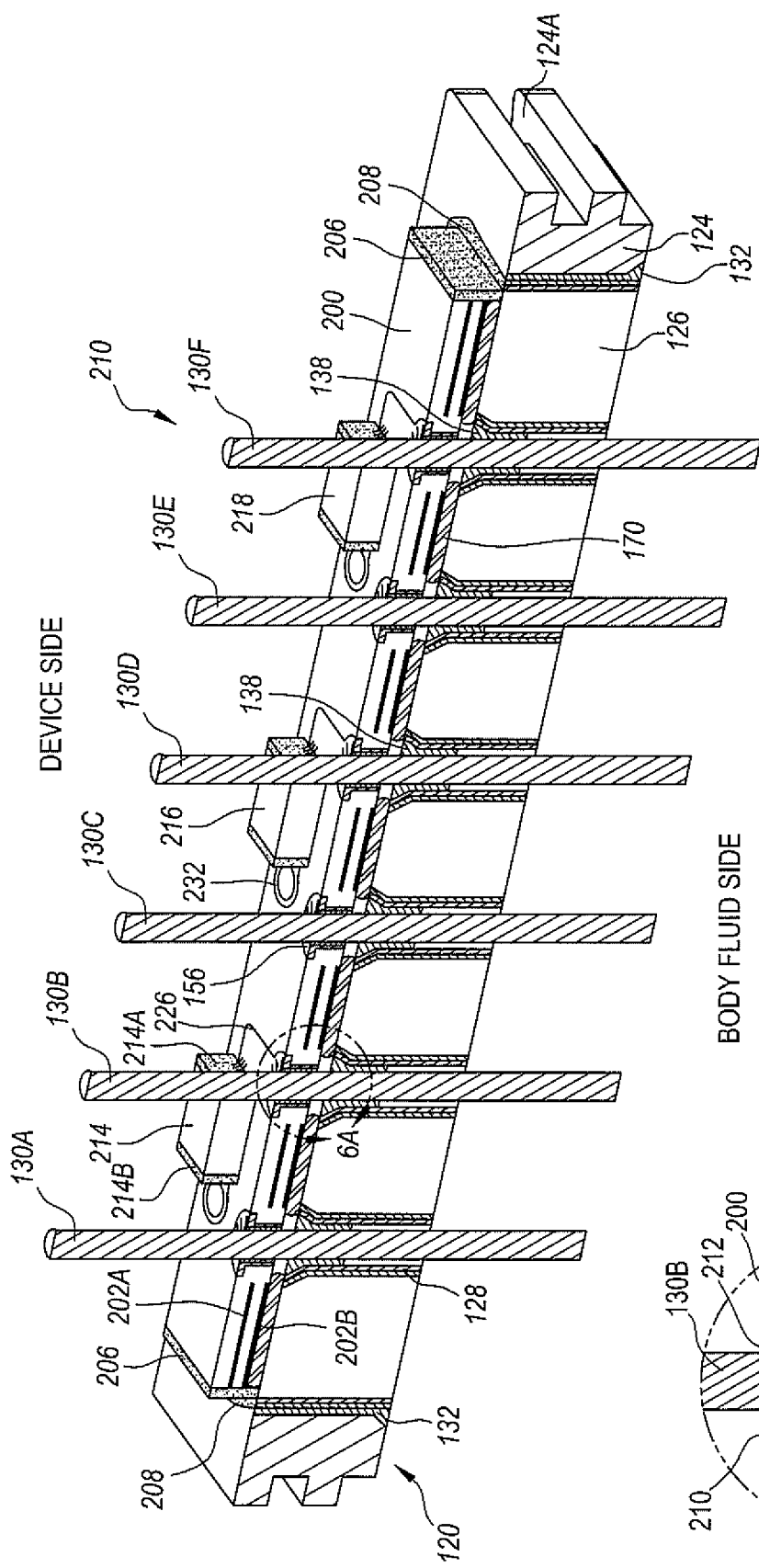

SELF-CENTERING POLYMERIC WASHER THAT PREVENTS MISALIGNMENT WHEN POSITIONED BETWEEN A FEEDTHROUGH AND A CIRCUIT BOARD SUPPORTING EMI FILTER CAPACITORS FOR A MEDICAL DEVICE

CROSS-REFERENCE TO RELATED APPLICATION

This application is a continuation-in-part of U.S. application Ser. No. 18/377,609, filed on Oct. 6, 2023.

BACKGROUND OF THE INVENTION

1. Field of the Invention

The present invention generally relates to medical devices. More particularly, the present invention describes a self-centering polymeric or ceramic washer that is positioned between a hermetic feedthrough and a circuit board supporting a plurality of filter capacitors for a medical device, for example, an active implantable medical device.

2. Prior Art

A polymeric washer for use in filtered feedthrough assemblies is typically made from a relatively lubricious polymeric material. However, lubricious (slippery) polymeric washers are particularly problematic with regards to centering their openings about a plurality of terminal pins of the feedthrough. Even if the polymeric washer has an adhesive coated on each of its opposed sides, because the washer must be applied and laminated to adjacent structures under significant pressure and high temperature, the washer can easily slide into a misaligned position with respect to the gold braze that hermetically seals each of the terminal pins extending through the via holes in the feedthrough insulator.

Moreover, the problem of inadvertent misalignment as a washer is being applied and laminated to adjacent structures under pressure and high temperature is not unique to a polymeric washer. A ceramic washer, even one that has an adhesive coated on each of its opposed sides, can also be prone to sliding out of proper alignment as it is being laminated between the insulator of a feedthrough and an EMI filter capacitor or a circuit board supporting a plurality of EMI filter capacitors.

Accordingly, a self-centering polymeric or ceramic washer that is configured to reside between a feedthrough and an EMI filter capacitor or a circuit board supporting a plurality of EMI filter capacitors and that has a number of shaped openings to prevent the washer from inadvertent lateral movement out of alignment on the feedthrough insulator is needed.

BACKGROUND OF THE INVENTION

The present invention relates to a feedthrough assembly that is attachable to a circuit board to form an assembly for incorporation into an active implantable medical device (AIMD). The feedthrough assembly comprises a polymeric or ceramic self-centering washer that is disposed between a feedthrough and a circuit board that supports a plurality of filter capacitors, for example MLCC chip capacitors or X2Y attenuator capacitors.

The self-centering washer has shaped openings through which terminal pins of the hermetic feedthrough extend. For example, with a feedthrough having first and second terminal pins, one embodiment of the self-centering washer has respective first and second shaped openings. The first shaped opening has a first inner arcuate or curved portion that contacts the first terminal pin and a first outer perimeter portion that is spaced from the first terminal pin. The first outer perimeter portion exposes a portion of the first braze hermetically sealing the first terminal pin to the insulator in an insulator first via hole. Similarly, the second shaped opening in the self-centering washer has a second inner arcuate or curved portion that contacts the second terminal pin and a second outer perimeter portion that is spaced from the second terminal pin. The second outer perimeter portion exposes a portion of the second braze hermetically sealing the second terminal pin to the insulator in an insulator second via hole.

Then, in an imaginary configuration having the first and second shaped openings superimposed one on top of the other, the cumulative arcuate distance measured in degrees of the respective first and second inner arcuate portions about one of the first and second terminal pins, subtracting overlap, results in a gap between the superimposed first and second shaped openings that is less than a diameter of either of the first and second terminal pins. That way, the polymeric or ceramic self-centering washer of the present invention is prevented from any lateral movement with respect to a device side of the insulator.

Preferably, the first and second inner arcuate portions of the first and second shaped openings each extend from about 90° to about 180° around the perimeter of the respective first and second terminal pins, and the first and second outer peripheral portions of the first and second shaped openings each extend from about 90° to about 180° around the perimeter of the respective first and second brazes. Further, the opposed ends of the inner arcuate portions meet opposed ends of the outer peripheral portions at rounded corners.

BRIEF DESCRIPTION OF THE DRAWINGS

FIG. 6 is a cross-sectional view showing a number of MLCC chip capacitors 214, 216 and 218 mounted on a circuit board 200 supported on a hermetically sealed feedthrough 120.

FIG. 6A is an enlarged view of the indicated section in FIG. 6.

DETAILED DESCRIPTION OF THE PREFERRED EMBODIMENTS

Figure 1:
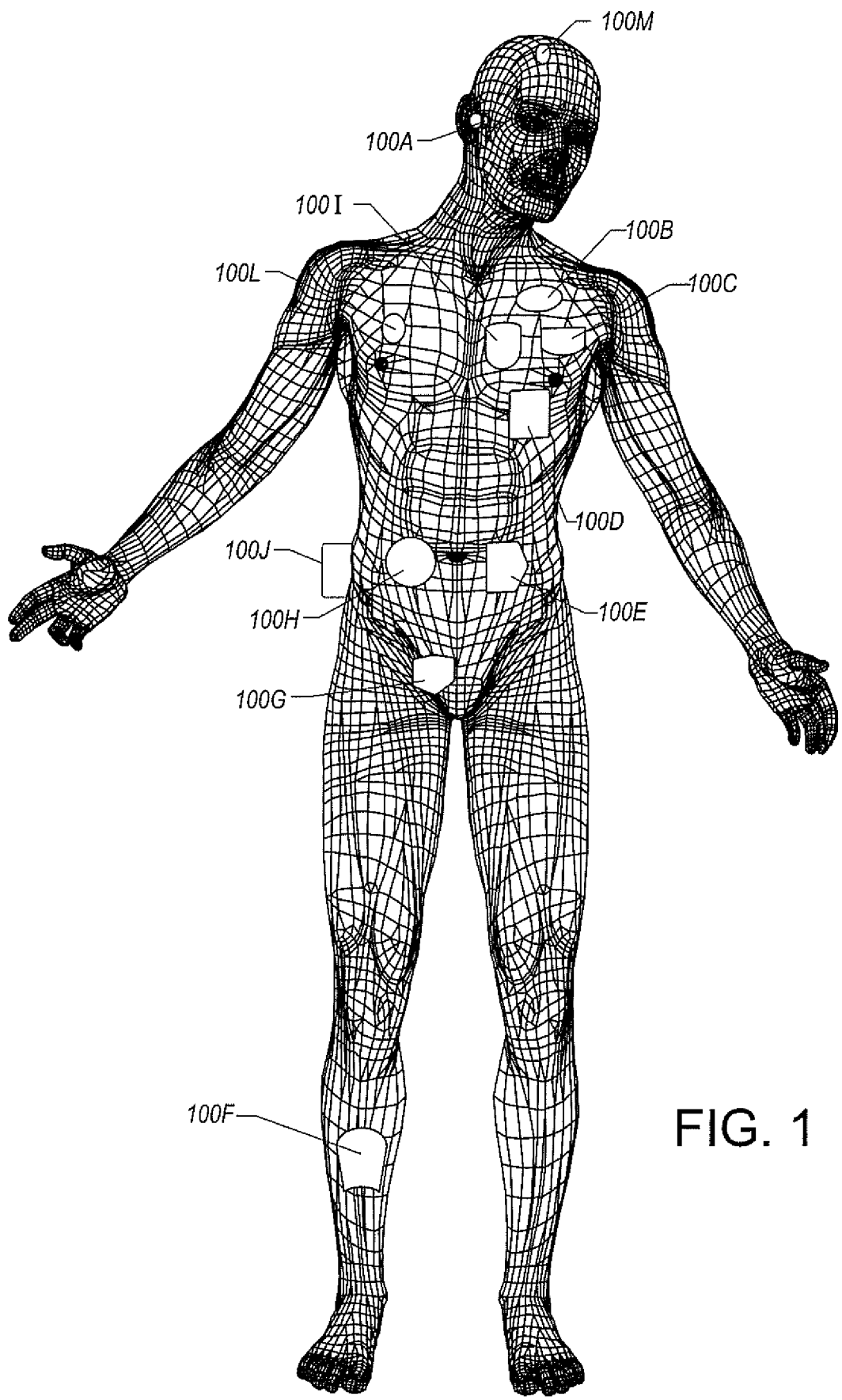
FIG. 1 is a wire formed diagram of a generic human body showing a number of medical devices 100A to 100L that can either be implanted in a patient's body or attached externally to the body.

FIG. 1 is a wireframe diagram of a generic human body showing a number of active medical devices. An active medical device has at least one power source and at least one electronic circuit.

Numerical designation 100A is a family of external and implantable hearing devices, which include the group of hearing aids, cochlear implants, piezoelectric sound bridge transducers and the like.

Numerical designation 100B includes the family of neurostimulators and brain stimulators. For example, neurostimulators are used to stimulate the Vagus nerve to treat epilepsy, obesity, and depression. Brain stimulators are similar to a pacemaker-like device and include electrodes implanted deep into the brain for sensing the onset of a seizure and also providing electrical stimulation to brain tissue to prevent the seizure from actually occurring. The leads that come from a deep brain stimulator are often placed using real-time imaging. Frequently, such leads are placed real-time using an MRI machine.

Numerical designation 100C shows a cardiac pacemaker, which is well-known in the art and may have either endocardial or epicardial leads. Implantable pacemakers may also be leadless (meaning without a lead or leads). The family of cardiac pacemakers 100C includes cardiac resynchronization therapy devices (CRT-P pacemakers) and leadless pacemakers. CRT-P pacemakers are unique in that they pace both the right and left sides of the heart. The cardiac device family also includes any and all types of biologic monitoring and/or data recording devices and all types of implantable loop recorders (ILR) or other such monitors and recorders of biologic activity, for example, an ILR that records the electrical activity of the heart.

Numerical designation 100D includes the family of left ventricular assist devices (LVAD's) and artificial hearts.

Numerical designation 100E includes the family of drug pumps, which can be used for dispensing of insulin, chemotherapy drugs, pain medications, and the like. Insulin pumps are evolving from passive devices to active devices that have sensors and closed loop systems, which can, for example, monitor blood glucose levels in real time. Such active pump devices tend to be more sensitive to EMI than passive pumps, which have no sense circuitry or externally implanted leads.

Numerical designation 100F includes a variety of external or implantable bone growth stimulators for rapid healing of fractures.

Numerical designation 100G includes urinary incontinence devices.

Numerical designation 100H includes the family of pain relief spinal cord stimulators and anti-tremor stimulators. Numerical designation 100H also includes the complete family of neurostimulators used to block pain signals.

Numerical designation 100I includes the families of implantable cardioverter defibrillators (ICD) and congestive heart failure (CHF) devices, including cardio-resynchronization therapy devices (CRT-D). A CRT-D, which is a special subcutaneous device for heart failure patients who are also at high risk for sudden cardiac death, can provide high-voltage defibrillation. The devices of numerical designation 100I may have either endocardial or epicardial leads.

Numerical designation 100J illustrates an externally worn pack, such as, but not limited to, an external insulin pump, an external drug pump, an external neurostimulator, a Holter monitor with skin electrodes or a ventricular assist device power pack.

Figure 2:
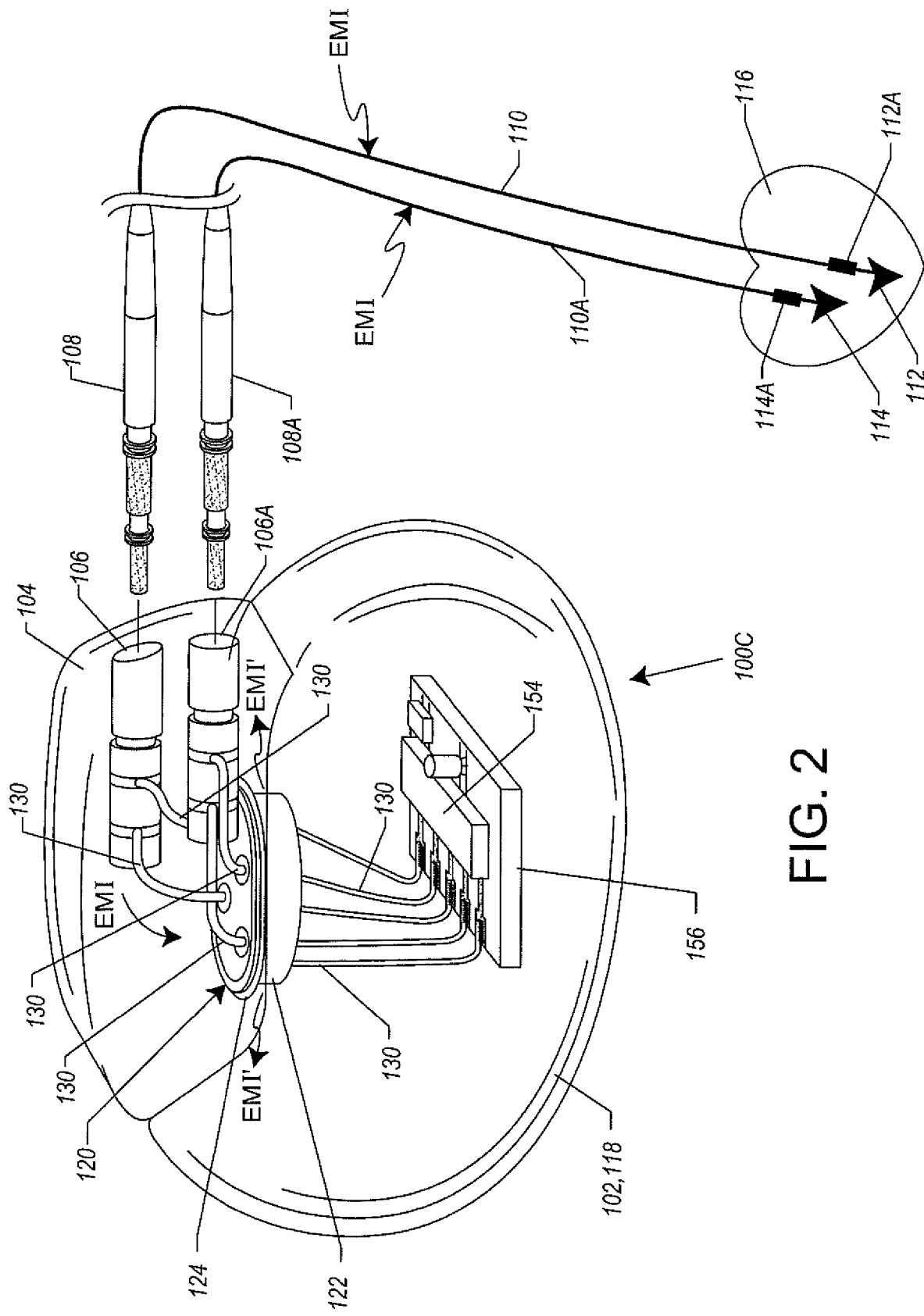
FIG. 2 illustrates a side cutaway view of the cardiac pacemaker 100C shown in FIG. 1.

FIG. 2 illustrates a side cutaway view of the cardiac pacemaker 100C shown in FIG. 1. The pacemaker electronics are housed inside a hermetically sealed AIMD housing 102 (typically titanium), which provides an electrically conductive electromagnetic shield. The header 104 is supported on the housing 102 and is typically made from a thermosetting plastic, such as Tecothane®. The header 104 houses one or more connector assemblies that are generally in accordance with ISO Standards IS-1, IS-2, IS4 or DF4. The connector assemblies comprise terminal blocks (female connectors) that are labelled 106, 106A. Electrical connectors 108, 108A (male connectors) are located at the proximal end of implantable leads 110, 110A. The electrical connectors 108, 108A are designed to be inserted into and mate with the female terminal blocks 106, 106A in the header 104. Distal and ring electrodes 112, 112A and 114, 114A are located at the distal end of the respective leads 110, 110A. The electrodes 112, 112A and 114, 114A are designed to contact body tissue, for example, the illustrated heart 116 to at least one of deliver electrical stimulation to the body tissue or sense biological signals from body tissue 116.

Further regarding FIG. 2, the AIMD housing 102 serves as a system ground 118 that provides the overall electromagnetic shield, and also functions as an otherwise dangerous EMI energy dissipating surface. The AIMD also has a hermetically sealed feedthrough 120 to which a quad-polar EMI filter capacitor 122 is mounted to thereby form a filtered feedthrough 123. Since the conductive ferrule 124 of the feedthrough 120 is electrically connected to the AIMD housing 102, the ferrule 124 of the feedthrough 120 is also part of the system ground 118. Accordingly, as illustrated, the system ground 118 illustrated in FIG. 2 includes the ferrule 124 and the device housing 102.

Figure 3:
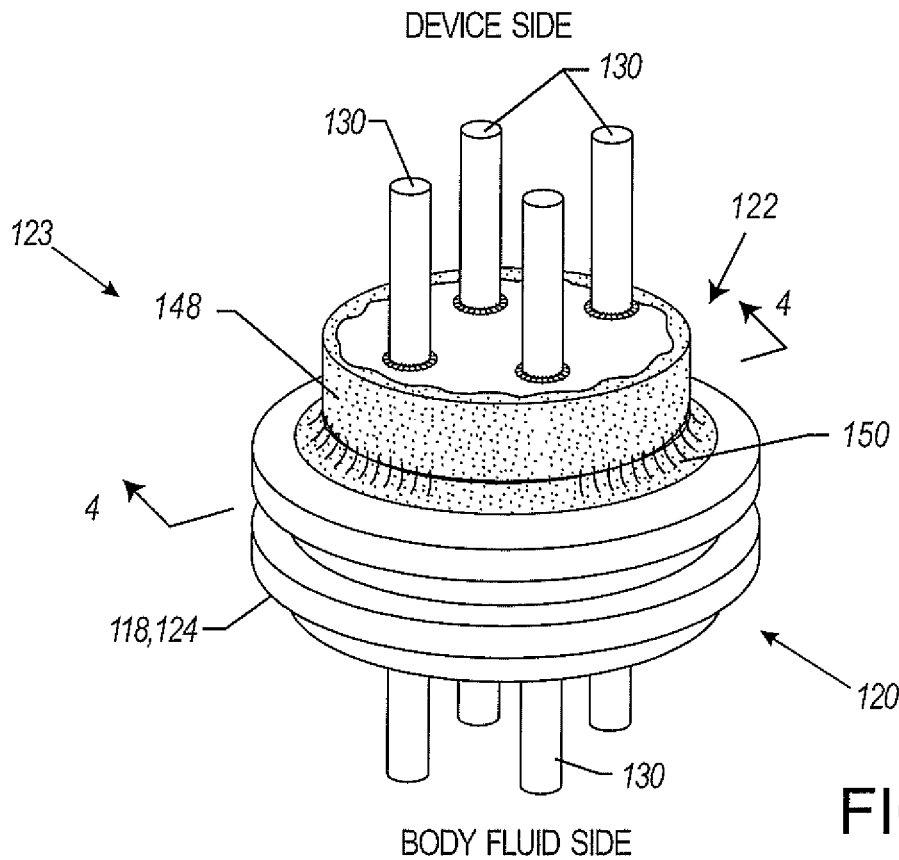
FIG. 3 is a perspective view of a filter feedthrough 123 comprising a quad-polar EMI filter capacitor 122 mounted on a hermetically sealed feedthrough 120.
Figure 4:
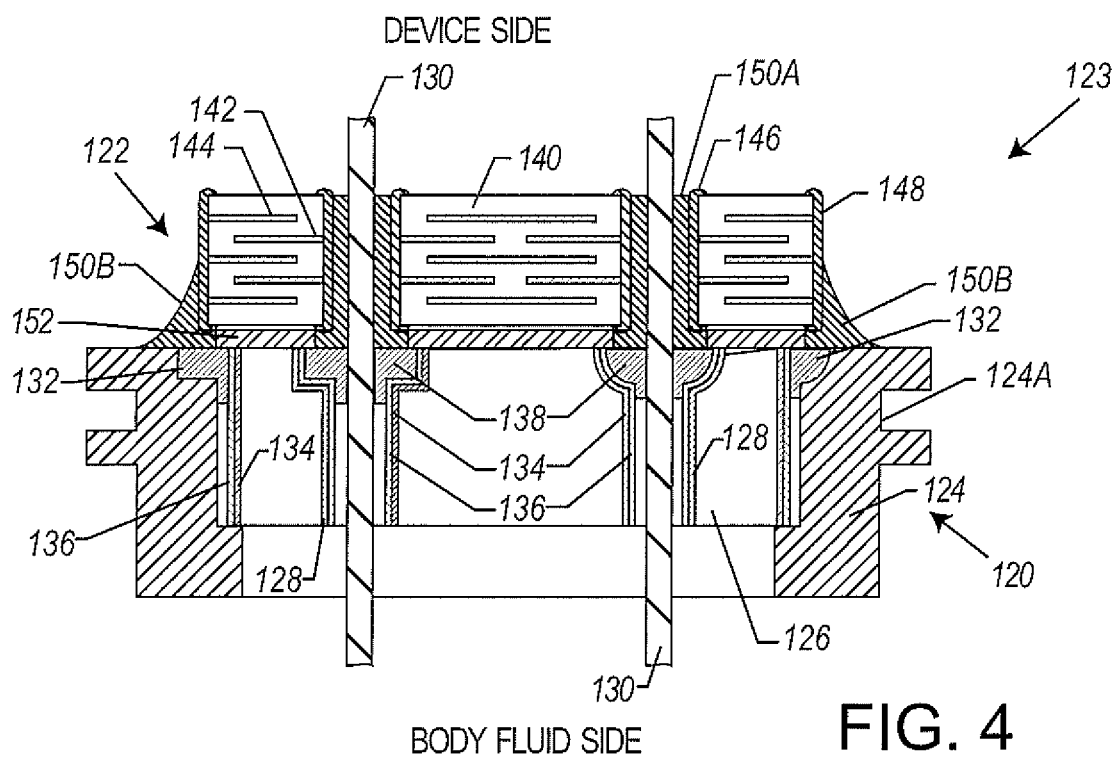
FIG. 4 is a cross-sectional view taken along line 4-4 of FIG. 3.

As shown in greater detail in FIGS. 3 and 4, the hermetic feedthrough 120 comprises the ferrule 124 having an opening in which a ceramic insulator 126 resides. The ferrule 124 has an H-flange 124A that serves to connect the feedthrough 120 to an opening in the device housing 102. The H flange 124A can comprise other shapes, as is known in the prior art. The insulator 126 has a number of via holes 128 through which terminal pins 130 extend. The insulator 126 also has an outer perimeter surface that is sized and shaped to reside inside the ferrule opening.

A ring-shaped braze 132, preferably a gold braze, hermetically seals the ferrule 124 to the outer perimeter surface of the insulator 126. However, before the insulator 126 is brazed to the ferrule 124, an adhesion layer 134 is directly applied to the outer surface of the insulator 126, and a wetting layer 136 is applied on top of the outer adhesion layer 134. The thusly prepared insulator 126 is then hermetically sealed to the ferrule 124 using the gold braze 132.

In a similar manner, an adhesion layer 134 is first directly applied to the inner surface of the insulator in the via holes, and the inner wetting layer 136 is applied on top of the inner adhesion layer 130. Then, ring-shaped gold brazes 138 hermetically seal the exemplary number of four terminal pins 130 to the insulator 126 in the via holes 128. In a preferred embodiment, the inner and outer adhesion layers 134 are titanium and the inner and outer wetting layers 136 are either molybdenum or niobium.

Still referring to FIGS. 3 and 4, the discoidal EMI filter capacitor 122 supported on the hermetic feedthrough 120 comprises a disc-shaped dielectric substrate 140 that supports a number of active electrode plates 142 that are interleaved in a partial overlapping arrangement with a number of ground electrode plates 144. The dielectric substrate 140 has an outer sidewall and internal passageways through which the terminal pins 130 extend. An active termination material 146 in the dielectric substrate passageways contacts the active electrode plates 142 and a ground termination material 148 on the dielectric substrate outer sidewall contacts the ground electrode plates 144. Then, an electrically conductive material 150A filled into the capacitor passageways connects the active electrode plates 142/active termination material 146 to the terminal pins 130. Similarly, an electrically conductive material 150B connects the ground electrode plates 144/ground termination material 148 to the ferrule 124. In a preferred embodiment, the electrical connection materials 150A, 150B are a polyimide, a solder, a thermal-setting conductive polymer such as a conductive epoxy, and the like.

A polymeric washer 152 resides between the feedthrough 120, particularly the insulator 126, and the discoidal EMI filter capacitor 122. The polymeric washer 152 is important because it helps prevent high voltage flashover, such as is possible in an implantable defibrillator application between terminal pins of opposite polarity and between an active terminal pin and the system ground including the conductive ferrule 124 of the feedthrough 120 which is electrically connected to the AIMD housing 102.

When the external capacitor metallization or ground termination material 148 of the discoidal filter capacitor 122 is electrically connected to the ferrule 124 of the hermetically sealed feedthrough 120, and the ferrule 124 in turn is hermetically sealed (typically by welding, such as laser welding) to the conductive housing 102 of an AIMD, for example, a cardiac pacemaker 100C, then the external capacitor ground termination material 148 is also electrically connected to the system ground 118. This means that the external capacitor ground termination material 148, the ferrule 124 and the AIMD housing 102 are all at the same ground potential and are all part of the overall AIMD equipotential surface (in other words, system ground 118). Since the hermetically sealed enclosure of the AIMD blocks EMI from entering inside the device housing 102, it is commonly known as an EMI shield or a Faraday cage.

Additionally, the discoidal EMI filter capacitor 122 is designed to selectively redirect undesirable high-frequency energy before it enters the AIMD housing 102 to this equipotential surface for diversion and/or energy dissipation. Ideally, the role of the feedthrough EMI filter capacitor 122 is designed to let low frequency biologic signals, such as therapeutic pacing pulses, freely pass without attenuation, while at the same time diverting dangerous high-frequency EMI energy to the AIMD housing 102 serving as an equipotential surface. The term "low frequency" refers to frequencies that range from a few hertz to kilohertz. Higher frequencies include about 1 MHz to about 200 MHz, which is in the range of the RF pulsed frequencies of 1.5 Tesla (64 MHZ) and 3 Tesla (128 MHZ) MRI scanners. The EMI filters of the present invention attenuate MRI RF frequencies very effectively.

When undesirable EMI energy is diverted to the AIMD housing 102, the undesirable EMI energy is dissipated harmlessly as a few milliwatts of heat energy (for an MRI scanner this can also be a few watts which is also harmless). In this manner, dangerous EMI energy is prevented from entering the AIMD housing 102 before the EMI energy can reach sensitive AIMD circuitry 154 mounted on the circuit board 156 (FIG. 2) housed inside the device housing 102. Should EMI energy undesirably enter inside the device housing 102, it could seriously disrupt the proper operation of the various AIMD circuits 154. Such EMI disruption could inadvertently suspend therapy, which could be immediately life threatening.

Figure 5:
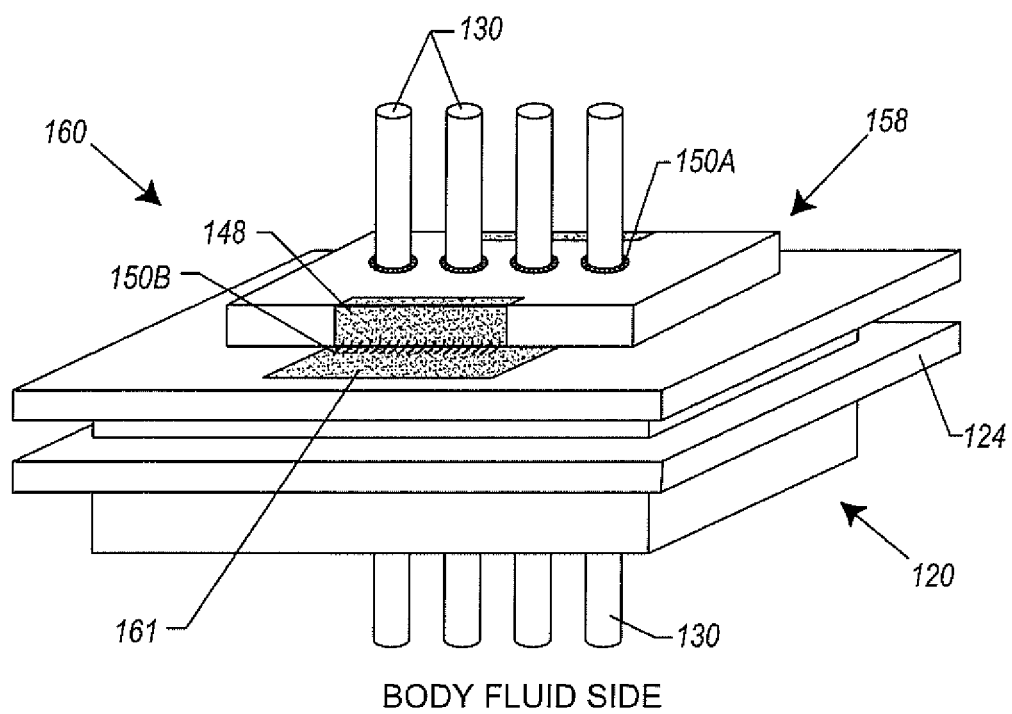
FIG. 5 is a perspective view of a filter feedthrough 123 comprising an inline quad-polar EMI filter capacitor 158 mounted on a hermetically sealed feedthrough 120.

FIG. 5 illustrates an inline quad-polar EMI filter capacitor 158 mounted on the previously described hermetically sealed feedthrough 120 to thereby form a filtered feedthrough 160. With the exception that it has a rectangular shape and not the disc-shape of the discoidal EMI filter capacitor 122 shown in FIGS. 3 and 4, EMI filter capacitor 158 is similar to the previously described discoidal EMI filter capacitor 122. Electrical connection material 150B connects the filter capacitor ground metallization 148 connected to ground electrode plates to the ferrule 124, which is generally of titanium. The ground electrical connections are desirably very low impedance and very low resistance. In this design, the ground electrical connection material 150B is connected to a gold bond pad 161, which forms an oxide-resistant electrical connection to the ferrule 124. Oxide-resistant EMI filter connections are described in U.S. Pat. No. 6,765,779, which is assigned to the assignee of the present invention and incorporated herein fully by reference. U.S. Pat. Nos. 9,427,596, 9,931,514, 10,350,421, 11,241,581, 11,344,734, and 11,633,612 also teach oxide-resistant low impedance electrical connections to a titanium ferrule and are also fully incorporated herein by reference. While not shown in the drawing of FIG. 5, a polymeric washer, similar to the washer 152 shown in FIG. 4, resides between the feedthrough 120, particularly the insulator 126, and the inline quad-polar EMI filter capacitor 158.

Turning now to FIG. 6, an EMI filter circuit board 200 is shown supported on the device side of the previously described hermetic feedthrough 120. The filter circuit board 200 is supported on the device side of the insulator 126 and has at least one ground plate 202, which can be an internal ground plate 202A or an external ground plate 202B. If external, the ground plate 202B is positioned adjacent to the device side of the insulator 126. It is within the scope of the present invention that the circuit board 200 can support more than one internal ground plate 202A as well as the external ground plate 202B. If desired, some or all of the external ground plate 202B and the internal ground plate 202A can be replaced by ground circuit traces. Various types of circuit boards and grounding techniques are more thoroughly described in U.S. Pat. No. 8,195,295, which is assigned to the assignee of the present invention and incorporated herein by reference.

The circuit board internal and external ground plates 202A, 202B are grounded to the ferrule 112 in an oxide resistant manner. A metallization 206 contacted to the opposed edges of the circuit board 200 contacts the internal and external ground plates 202A, 202B. Then, an electrically conductive material 208, for example, a polyimide, a solder, a thermal-setting conductive polymer such as a conductive epoxy, and the like, electrically connects the edge metallization 206 to the gold braze 132 hermetically sealing the insulator 126 to the ferrule 124. In that manner, the circuit board ground plates 202A, 202b are connected to the system ground 118 comprising the ferrule 124 and the device housing 102.

The circuit board 200 also has a number, for example six, passageways through which terminal pins 130A to 130F extend. The terminal pins 130A to 130F are sufficiently long so that a proximal pin portion extends outwardly beyond the device side of the circuit board 200 and a distal pin portion extends outwardly beyond a body fluid side of the insulator 126. The terminal pins 130A to 130F are secured in their respective passageways using a metal eyelet 210 and an electrically conductive material 212 that connects the eyelet to the terminal pin (FIG. 6A). The electrically conductive material 212 can be a polyimide, a solder, a thermal-setting conductive polymer such as a conductive epoxy, and the like.

FIG. 6 further shows that there are a number of MLCC chip capacitors 214, 216 and 218 mounted on the device side of the circuit board 200. The MLCC chip capacitors each have an active termination spaced from a ground termination. As particularly shown in FIGS. 16 and 16A to 16C, exemplary MLCC chip capacitor 214 comprises a dielectric substrate 220 that supports a plurality of active electrode plate 222 interleaved in a capacitive relationship with a plurality of ground electrode plates 224. The active electrode plates 222 are connected to an active termination 214A spaced from a ground termination 214B that is connected to the ground electrode plates 224. The other MLCC chip capacitors 216 and 218 shown in FIG. 6 have a similar structure.

As shown in FIGS. 6 and 6A, a circuit trace 226 connects from the active termination 214A for MLCC chip capacitor 214 to a metal insert 210. The metal insert 210 is connected to terminal pin 130B by an electrically conductive material 212, for example, an electrically conductive epoxy or solder.

Figure 6C:
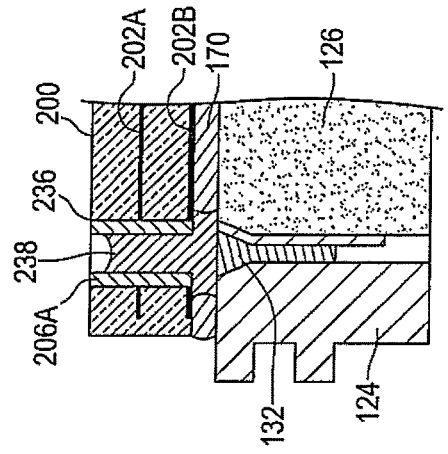
FIG. 6C illustrates that the ground pin of FIG. 6B can be replaced by a ground via 236 that is spatially aligned over the hermetic seal to ferrule gold braze 132.
Figure 6E:
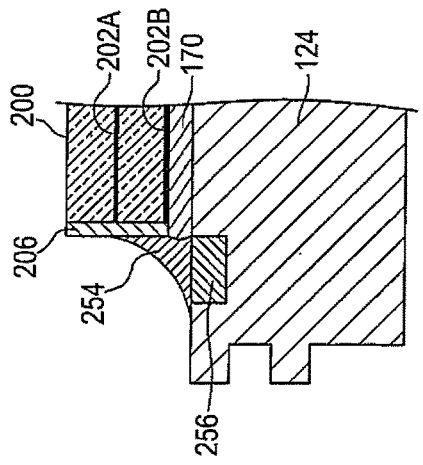
FIG. 6E illustrates that the circuit board 200 of FIG. 6 can have a ground edge metallization 206 that is connected to a gold pocket-pad 256, which is formed into a recess in the ferrule 124.
Figure 6B:
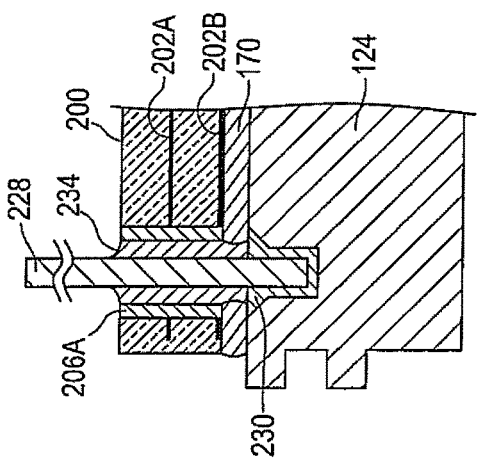
FIG. 6B is a partial cross-sectional view of a ground terminal pin 228 welded or brazed 230 into an opening in the ferrule 124 and connected to the circuit board ground plates 202A, 202B by an electrically conductive material 234.

FIG. 6B is a cross-sectional view illustrating an embodiment of the circuit board 200 having a ferrule ground pin 228 that is electrically and mechanically connected to the ferrule 124 by a gold braze or a laser weld 230. Ideally, ground pin 228 is of an oxide-resistant material, such as, but not limited to, platinum. This makes for an essentially oxide-free electrical connection 234 to a circuit board via metallization 206A connected to the internal and external ground plates 202A, 202B.

Still referring to FIG. 6B, one will see that the circuit board via hole metallization 206A is spatially aligned over the gold braze or a laser weld 230. Throughout the present invention, via holes are provided with some sort of a conductive or metallization layer on the inside diameters. It is understood by one skilled in the art that the inside diameter of circuit board via holes can be metal eyelets, plated, metallized, or the like. In each case, the conductive or metallization layer of the via hole is electrically connected to one or more internal or external circuit board ground plates or circuit traces. In the case of FIG. 6B, the circuit board metallization 206A makes electrical contact to the internal and external circuit board ground plates 202A, 202B. In the case where the ground pin 228 is of a lower cost material such as tantalum, niobium or titanium, then the gold braze or laser weld 230 must be exposed such that electrical connection material 234 can contact termination 206A and the gold braze or laser weld 230 thereby forming an oxide resistant low impedance connection.

FIG. 6C illustrates an alternative embodiment of how the circuit board ground plates 202A, 202B are grounded to the ferrule 124. In this case, a circuit board ground via hole 236 is spatially aligned over the gold braze 138 that hermetically seals the insulator 126 to the ferrule 124. By spatially aligning the ground via hole 236 over the gold braze 132, an essentially oxide-free electrical connection directly to the hermetic seal gold braze is made using electrical connection material 238. Electrical connection material 238 can be a solder, a thermal-setting conductive adhesive, and the like.

Figure 6D:
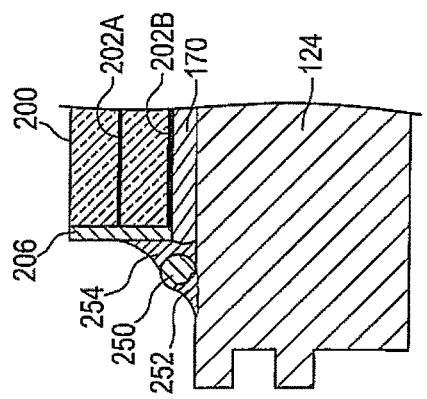
FIG. 6D illustrates that the circuit board 200 of FIG. 6 may have an edge metallization 206 that is attached to a metal addition 250, which is laser welded or gold brazed 252 to the ferrule 124.

FIG. 6D shows that an oxide-free electrical connection to the circuit board ground plates 202A, 202B can also be achieved by an oxide-resistant metal addition 250, which is either gold brazed, or laser welded 252 to the ferrule 124. Typically, this metal addition 250 is of an oxide-resistant material, such as platinum. The metal addition 250 is connected to the circuit board edge metallization 206 by an electrical connection material 254.

FIG. 6E illustrates another method of forming an oxide-resistant electrical connection from the circuit board ground plates 202A, 202B to the ferrule 124. In this case, there is a gold pocket-pad 256, which acts like a swimming pool moat into which a gold braze, or equivalent material is formed. This forms an oxide-resistant electrical connection between the ferrule 124 and the electrical connection material 254 connected to the circuit board ground edge metallization 206 and, in turn, to the circuit board ground plates 202A, 202B.

Figure 6G:
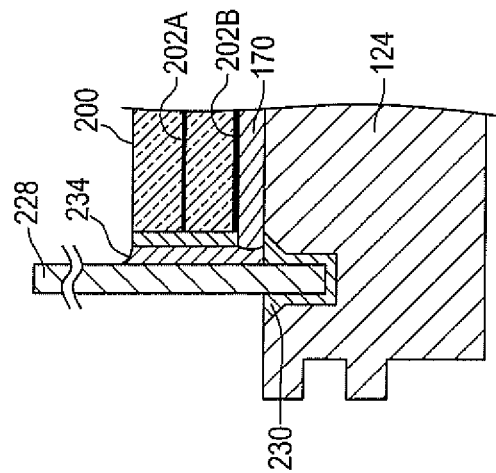
FIG. 6G illustrates that the circuit board 200 may have an edge ground metallization 206 that is conductively coupled to the oxide-resistant ground pin 228 shown in FIG. 6B.
Figure 6F:
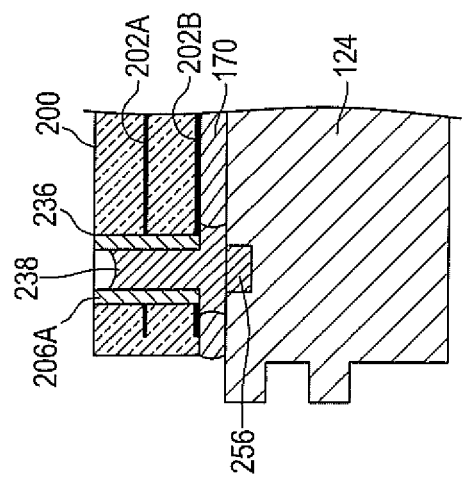
FIG. 6F is similar to FIG. 6E, except that the ground via hole 236 is spatially aligned over a gold pocket-pad 256 formed in a ferrule recess.

FIG. 6F is very similar to FIG. 6E in that an oxide-resistant gold bond pad 256 has been provided in a ferrule pocket. In this case, the circuit board ground via hole 236 has been spatially aligned over the gold pocket-pad 256, such that an electrical connection 238 is made to the oxide-resistant noble gold filling the pocket. In this way, the circuit board ground plates 202A, 202B have a very low resistance connection to system ground 118, which is the ferrule ground 124 connected to the device housing 102. Gold pocket-pads are disclosed in U.S. Pat. No. 10,350,421, the contents of which are incorporated fully herein by this reference. Gold pocket-pads may comprise other oxide-resistant materials such as platinum. Noble metals, such as gold and platinum, are used as jewelry for this reason, as gold and platinum do not tarnish or oxidize over time. The pocket-pad 256 may comprise a number of other oxide-resistant materials, such as gold, gold alloys, rhodium, rhodium alloys, platinum, platinum alloys, platinum-iridium alloys, palladium, palladium alloys, nitinol, cobalt-chromium alloys, and combinations thereof.

FIG. 6G is similar to FIG. 6B in that there is an oxide-resistant ground pin 228, which is electrically and mechanically connected to the ferrule 124 by a laser weld or a gold braze 230 (gold brazes and laser welds burn through any oxide on the titanium ferrule forming a very stable and low resistance connection). In this case, instead of grounding through a via hole, as illustrated in FIG. 6B, there is an electrical connection 234 from the circuit board ground edge metallization 206 directly to the oxide-resistant ground pin 228. Accordingly, this provides a very low equivalent series resistance (low ESR) grounding path to system ground 118. As previously defined, system ground 118 comprises the ferrule 124 connected to the device housing 102. Importantly, the circuit board ground plates 202A, 202B provide a low impedance path for the EMI filters (an MLCC chip capacitor 214, an X2Y attenuator 240 shown in FIGS. 16 and 16A to 16C, and combinations thereof) to divert dangerous EMI currents while at the same time shielding the insulator 126 from direct penetration of high frequency RE-radiated noise (EMI).

Referring again to FIGS. 6 and 6B to 6G, the circuit board ground plates 202A, 202B can also be called circuit board ground shield plates. In other words, the ground plates 202A, 202B not only provide a low impedance filter circuit diversion pathway to system ground, but they also shield against EMI radiated energy from penetrating through the hermetic seal insulator 126 such that it could undesirably enter into the device housing 102. Circuit board shield plates or ground plates act in an identical manner. Not shown is that these plates also absorb incident RF energy and that the capacitive action of the filter diverts the RF energy to the AIMD housing 102, where it is harmlessly dissipated as a few milliwatts of heat energy. This diversion prevents the EMI from dangerously reaching the inside of the AIMD shielded housing 102.

Referring back to FIG. 6, the ground termination 214B for the MLCC chip capacitors is electrically connected to the ground plates 202A and 202B through a metal insert 232 that resides in a circuit board ground via. This metal insert 232 extends into the circuit board 200 to the depth of the ground plate, whether there is only an internal ground plate 202A, only an external ground plate 202B or both internal and external ground plates 202A, 202B.

It bears mentioning that six terminal pins 130A, 130B, 130C, 130D, 130E and 130F are present in circuit board 200 depicted in FIG. 6, but because of the cross-section, only three MLCC chip capacitors 214, 216 and 218 are illustrated. This drawing is a cross-sectional view of the assembly so the other three MLCC chip capacitors connected to active terminal pins 130A, 130C and 130E are not shown because they are mounted on the portion of the circuit board 200 that has been cut off by the cross-section. Nonetheless, MLCC chip capacitors 214, 216 and 218 are integral to the illustrated assembly. MLCC chip capacitor EMI filters are more thoroughly described in U.S. Pat. No. 8,195,295, which is assigned to the assignee of the present invention and incorporated herein by reference. Six active terminal pins 130A, 130B, 130C, 130D, 130E and 130F are just one illustration, as there can be any number of terminal pins depending on the particular active medical device design.

Figure 17:
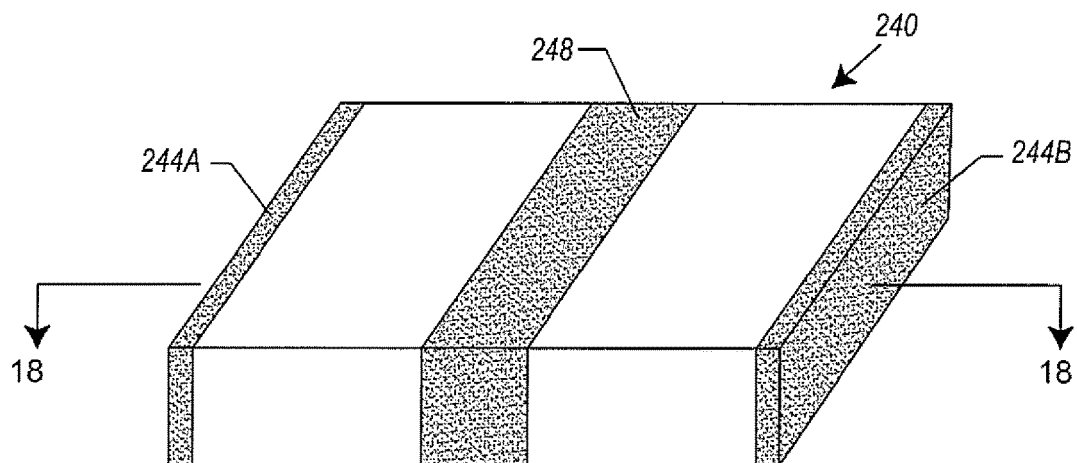
FIG. 17 is a perspective view of an X2Y attenuator 240 that is useful in lieu of the MLCC chip capacitors 214 to 218 mounted on the circuit board 200 shown in FIG. 6.
Figure 18:
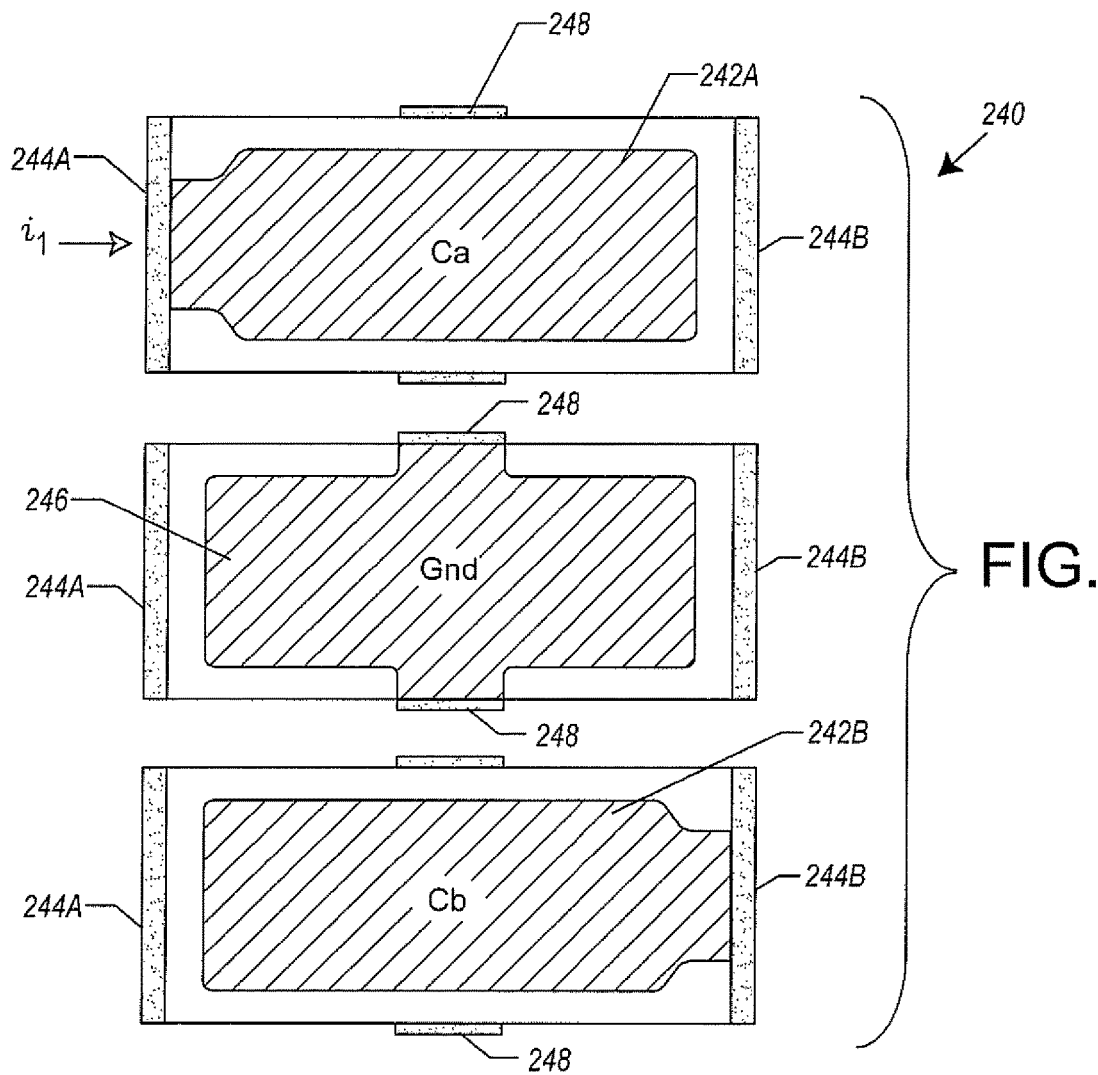
FIG. 18 is a sectional view taken along line 18-18 of FIG. 17.

In lieu of the MLCC chip capacitors 214 to 218 mounted on the circuit board 200 illustrated in FIG. 6, it is within the scope of the present invention that all or some of those capacitors can be replaced by X2Y attenuators. An exemplary bipolar X2Y attenuator 240 is illustrated in FIGS. 17 and 18. Bipolar means that the X2Y attenuator 240 can filter two leadwires at the same time. This is better understood by examining the internal active electrode plates 242A and 242B of FIG. 18. The left-side active electrode plates 242A are connected to the left side active capacitor metallization 244A. The right-side active electrode plates 242B are connected to the right-side active capacitor metallization 244B. The active electrode plates 242A, 242B are interleaved with at least one ground electrode plate 246.

It is appreciated that any number of active and ground electrode plates can be interleaved to create a desired line-to-line or a line-to-ground amount of capacitance or filtering. For example, if a relatively large amount of line-to-line filtering (known as differential mode filtering) is desired, that is, filtering between active capacitor electrodes 242A (Ca) and 242B (Cb), then the interleaved ground electrode plate 246 is reduced in size (can be almost eliminated), which thus increases the effective capacitance area (ECA) between the two opposed active electrode plates 242A (Ca) and 242B (Cb). However, if mostly line-to-ground filtering is desired (known in the art as common mode filtering), filtering is from both active electrodes 242A (Ca) and 242B (Cb) to an enlarged ground electrode plate 246 (Gnd) metallization 244A. The continuous ground metallization 248 is shown as a metallization band that is disposed all the way around the X2Y attenuator 240. However, the ground metallization 248 can also be discontinuous as long as it electrically connects all of the ground plates to each other.

Simultaneous filtering of two feedthrough leadwires is possible because the active electrode plates 242A and 242B of the X2Y attenuator 240 are designed such that the X2Y attenuator essentially comprises two different capacitors, one capacitor comprising the active electrode plates 242A electrically connected to the active metallization 244A and a second capacitor comprising the active electrode plates 242B electrically connected to the active metallization 244B. Each active electrode plate 242A, 242B sandwiched by the ground electrode plates 246 is connected to its respective active metallization 244A and 244B. This means that the active electrode plates 242A, 242B are electrically connectable to two of the leadwires 130A to 130F of the EMI filtering circuit board 200. As such, one leadwire 130A to 130F is electrically connectable in pairs to the active electrode metallization 244A and a second one of the leadwires 130A to 130F is electrically connectable to the active electrode metallization 244B.

Figure 7:
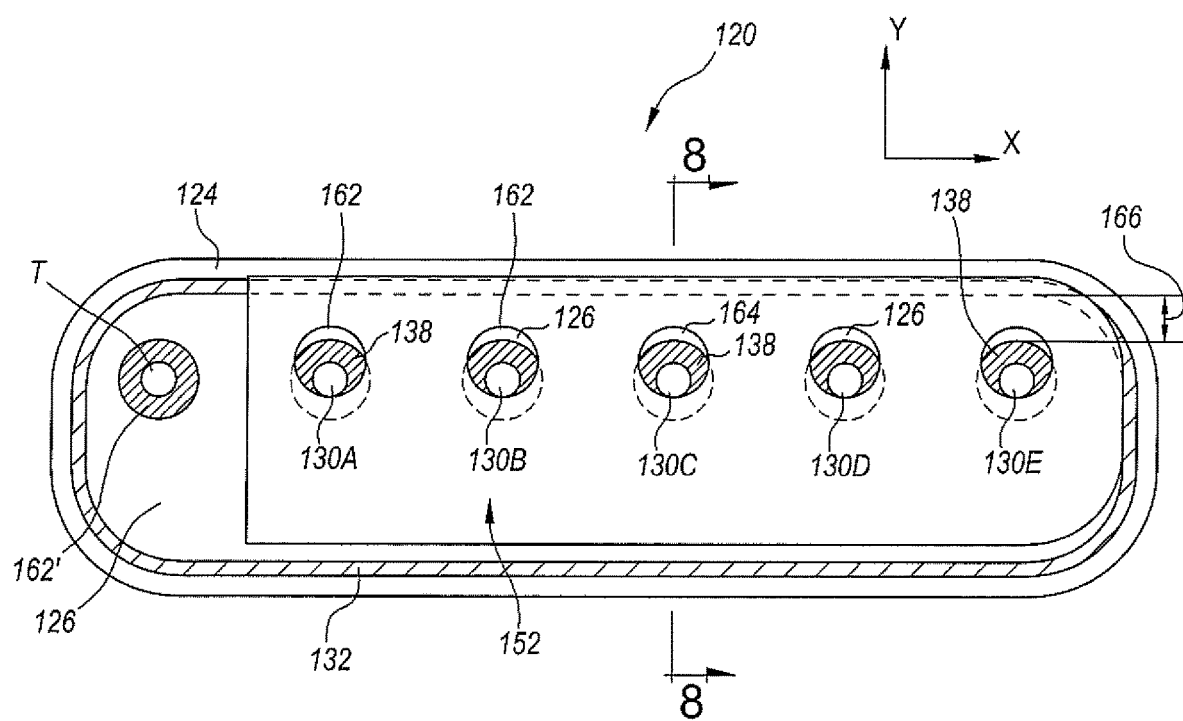
FIG. 7 is a plan view of a hermetically sealed feedthrough 120 similar to the feedthroughs 120 shown in FIGS. 3 to 5 on which a prior art polymeric washer 152 is undesirably misaligned over gold brazes 138 for terminal pins 130A to 130E.

Referring now to FIG. 7, this drawing is a plan view of an exemplary polymeric washer 152 of the type that might reside between the feedthrough 120, particularly the insulator 126, and the discoidal EMI filter capacitor 122 in FIG. 4, between the feedthrough 120 and the inline quad-polar EMI filter capacitor 158 in FIG. 5, and between the feedthrough 120 and the circuit board 200 shown in FIG. 6. This drawing shows that the prior art polymeric washer 152 has round-shaped openings 162 (which is typical) for receiving the respective feedthrough terminal pins 130A to 130E. However, the round-shaped openings 162 let the washer 152 move along the upper surface of the feedthrough insulator 126 and out of a centered alignment with respect to the terminal pins 130A to 130E.

For example, using the x-y axis coordinate system shown in FIG. 7 for directional referencing, the polymeric washer 152 has undesirably moved upwardly along the y-axis so that a portion of the round-shaped openings 162 contact a lower side of the terminal pins 130A to 130E while an opposed portion of the washer openings 162 has slid past the insulator-to-ferrule braze 150B so that an adjacent portion of the insulator 126 is uncovered. The polymeric washer 152 can move in a myriad of undesirable misaligned directions along the insulator 126 including downwardly along the y-axis, to the left along the x-axis, or to the right along the x-axis. The problem is that when such sliding misalignment occurs, a portion of the feedthrough insulator 126 is left uncovered. That can lead to a high voltage flashover situation, such as is possible in an implantable defibrillator application between terminal pins of opposite polarity and between an active terminal pin and the system ground including the conductive ferrule 124 of the feedthrough 120 electrically connected to the AIMD housing 102.

Figure 8:
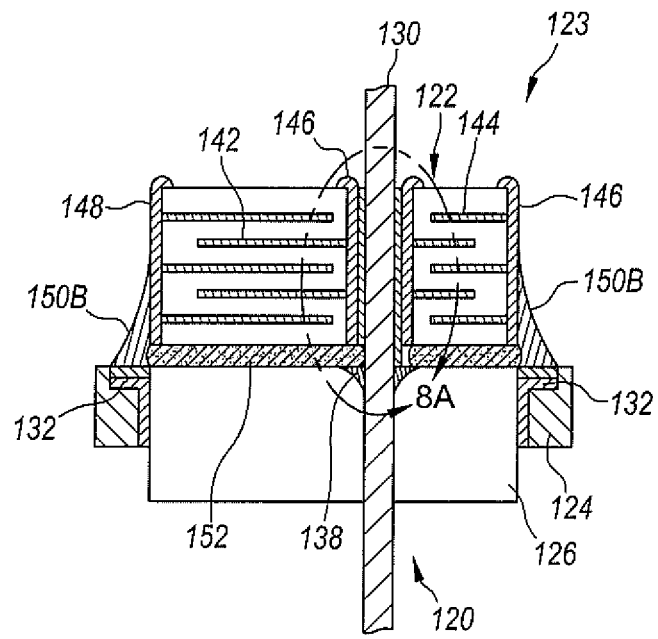
FIG. 8 is a cross-sectional view taken along line 8-8 of FIG. 7.
Figure 8A:
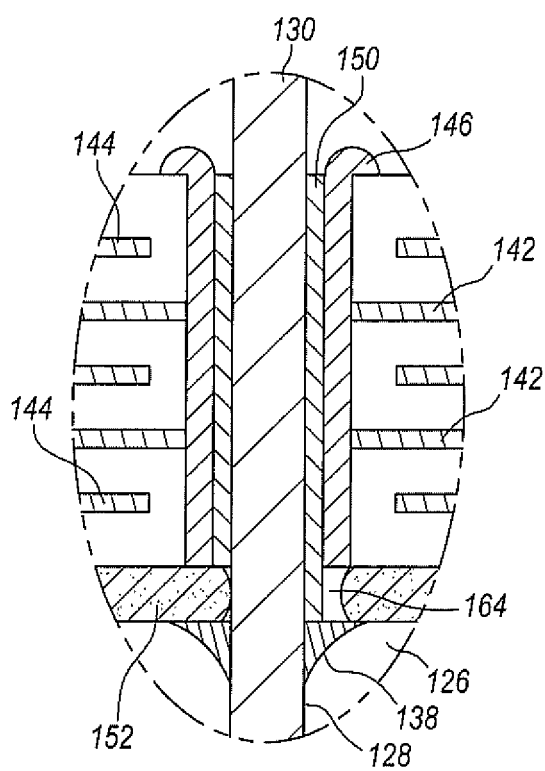
FIG. 8A is an enlarged view of the indicated section of FIG. 8.

The cross-sectional views of FIGS. 8 and 8A further illustrate undesirable misalignment along the planar surface of the feedthrough insulator 126 with respect to a representative one of the terminal pins 130. Misalignment of the polymeric washer 152 creates a gap 164 between the gold brazes 138 that hermetically seal the terminal pin 130 to the insulator 126 in the via hole 128 and the closest ground, which in this embodiment, is the ferrule gold braze 132. The gap 164 can result in the highly undesirable effect of reducing the high-voltage keep-out zone 166 (FIG. 7), which is also the flashover distance. The gap 164 can be particularly problematic when the feedthrough 120 is exposed to a high volts per mil (V/mil) stress. Partial delamination between the polymeric washer 152 and the feedthrough insulator 126 can create an air bubble between the positive and negative or active and ground poles, which can enable a voltage arc or avalanche. Moreover, the gap 164 within the keep-out zone 166 of the gold braze 132 can undesirably lead to a high-voltage discharge or a catastrophic avalanche discharge.

Commensurate with the amount of misalignment that exists, the misaligned polymeric washer 152 will also undesirably cover a portion of the insulator-to-ferrule gold braze 132. The covered portion of the gold braze 132 becomes unavailable for an oxide-resistant electrical connection.

It is noted that the telemetry pin T in the embodiment shown in FIG. 7 is not associated with a filter capacitor and is therefore not covered by the washer 152. The reason the polymeric washer 152 does not cover the telemetry pin T is because the telemetry pin cannot be filtered. RF telemetry requires a high frequency signal that will not communicate if it is filtered. Instead, the telemetry pin T enables high-frequency RF communication between an external AIMD programmer and the implanted AIMD. This means that the telemetry pin T must not have any electrical connection to an EMI filter capacitor 122 (FIGS. 3 and 4), an EMI filter capacitor 158 (FIG. 5) or an EMI filter circuit board 200 (FIG. 6). Otherwise, an RF telemetry signal travelling down the telemetry pin T would be undesirably attenuated. Moreover, the telemetry pin T is typically located in the header 104 (FIG. 2), which is outside the AIMD housing 102, and it is relatively small in comparison to the implantable leads 110, 110A (FIG. 2) or, the telemetry pin T is positioned in a separate area inside the AIMD. Accordingly, the telemetry pin T does not tend to pick up much EMI and, therefore, does not need EMI filtering.

Figure 9:
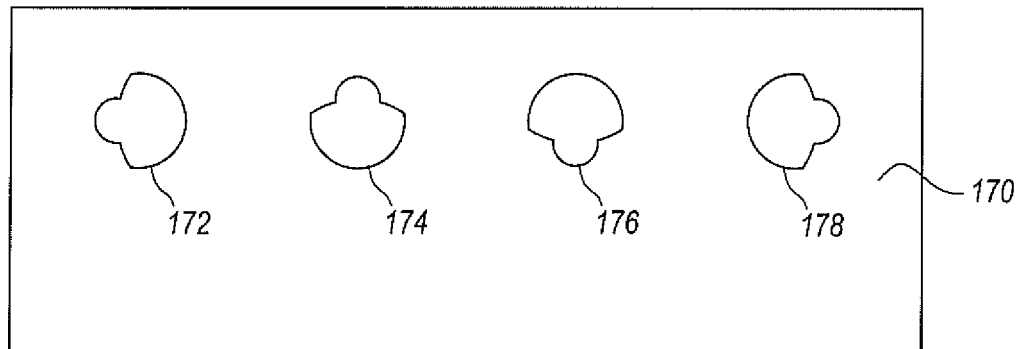
FIG. 9 is a plan view of a novel self-centering polymeric or ceramic washer 170 according to the present invention.

FIG. 9 is a plan view that illustrates one embodiment of a novel self-centering polymeric or ceramic washer 170 according to the present invention. The self-centering polymeric or ceramic washer 170 replaces the washer 152 shown in FIG. 7 and comprises four spaced-apart shaped openings 172 to 178 that extend through its thickness. As further shown in FIG. 10, the openings 172 to 178 are sized and shaped to receive a corresponding one of the terminal pins 130A to 130D of the feedthrough 120 shown in FIG. 5. Generally, the shaped openings 172 to 178 each comprise an opening inner arcuate portion that contacts the terminal pin and an opening outer perimeter portion that is spaced from the terminal pin and that exposes a portion of the braze hermetically sealing the terminal pin to the insulator in a via hole extending through the insulator 126.

Figure 10:
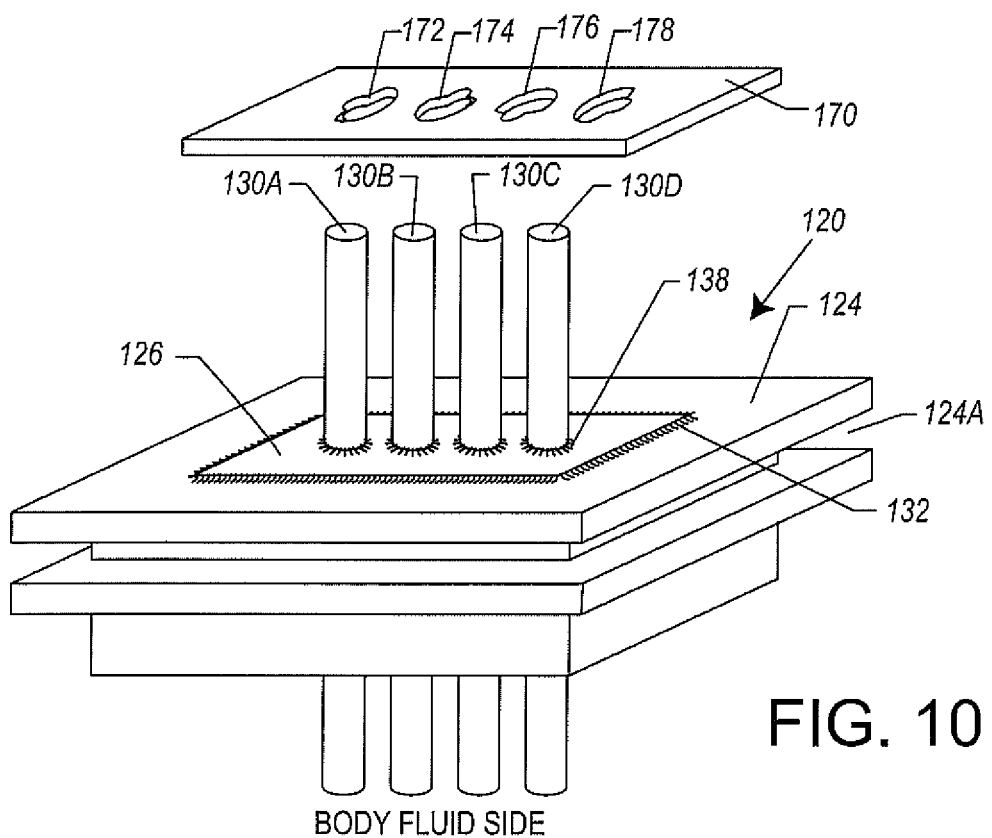
FIG. 10 is an exploded view of a filtered feedthrough 123 that is similar to that shown in FIG. 5 but including the novel self-centering polymeric or ceramic washer 170 shown in FIG. 9 mounted on the hermetically sealed feedthrough 120.

It is noted that while four openings 172 to 178 are provided in the polymeric or ceramic washer 170 shown in FIGS. 9 and 10, that is not intended to be a limitation of the present invention. A self-centering polymeric or ceramic washer according to the present invention will have as many spaced-apart openings as there are active terminal pins which will subsequently be connected to an EMI filter capacitor 122 (FIGS. 3 and 4), an EMI filter capacitor 158 (FIG. 5) or an EMI filter circuit board 200 (FIG. 6) that are designed to selectively redirect undesirable high-frequency energy before it enters the AIMD housing 102.

Figure 11:
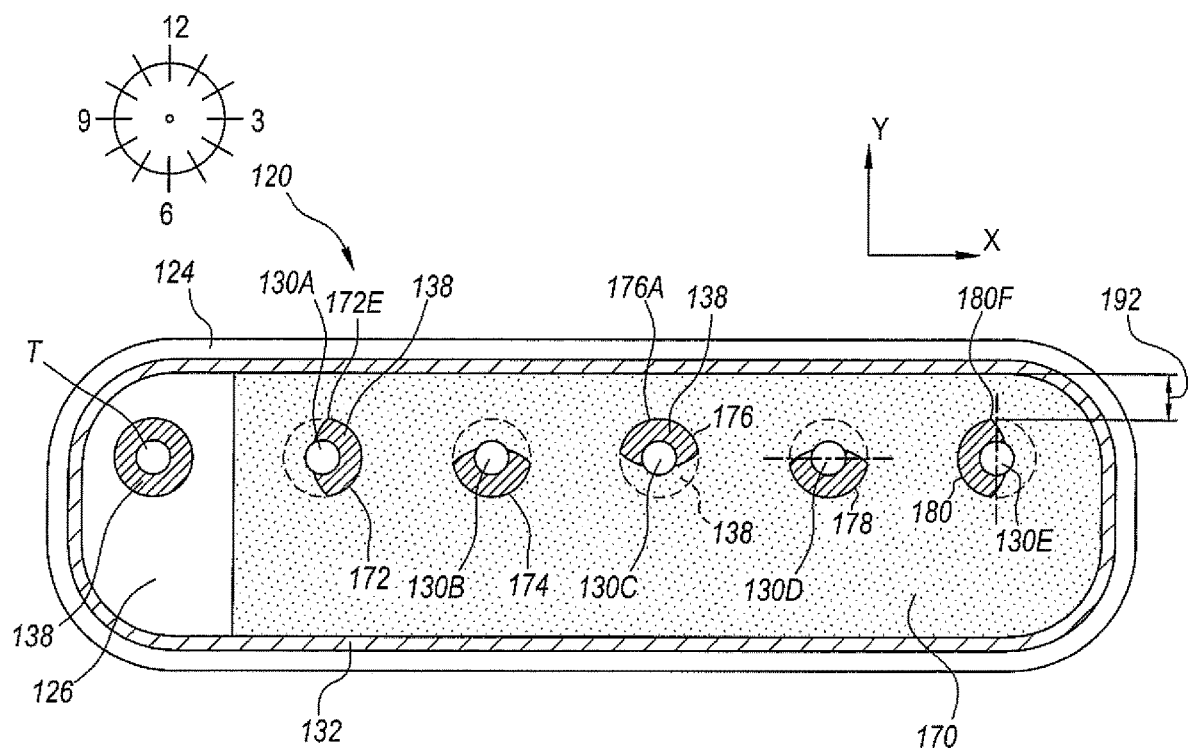
FIG. 11 is a plan view of a hermetically sealed feedthrough 120 on which the self-centering polymeric or ceramic washer 170 shown in FIGS. 9 and 10 is desirably located.

FIG. 11 is a plan view of the self-centering polymeric or ceramic washer 170 shown in FIGS. 9 and 10 mounted on top of the feedthrough 120 shown in FIGS. 3 to 6. As previously described, the telemetry pin T is not filtered, so the polymeric or ceramic washer 170 does not extend to that pin (although it could as long as the filter capacitor or filter circuit board does not contact the telemetry pin T).

FIGS. 11A, 11B, 11C and 11D are enlarged sectional plan views of the respective shaped openings 172, 174, 178 and 180 of the self-centering polymeric or ceramic washer 170. FIG. 11E is an enlarged sectional plan view illustrating the shaped openings 172 and 174 of respective FIGS. 11A and 11B superimposed one on top of the other. The reason for this will be described in detail hereinafter.

Figure 11A:
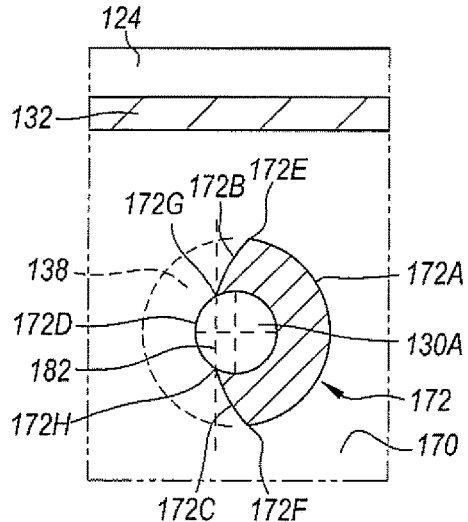
FIGS. 11A to 11D are sectional views of respective openings 172, 174, 176 and 180 of the polymeric or ceramic washer 170 shown in FIG. 11 self-centered about terminal pins 130A, 130B, 130C and 130E, respectively.

Looking first at opening 172 in FIG. 11A, it has an outer perimeter portion 172A that extends for about 90° to about 180° around the circular perimeter of the gold braze 138 which resides underneath the polymeric or ceramic washer 170 at the terminal pin 130A. The outer perimeter portion 172A extends to opposed inwardly extending upper and lower edges 172B and 172C that in turn meet an inner arcuate portion 172D. The inner arcuate portion 172D faces the outer perimeter portion 172A and extends for about 90° to about 180° around the circular perimeter of the terminal pin 130A. The outer perimeter portion 172A meets the upper curved edge 172B at junction 172E and the lower curved edge 172C at junction 172F. Further, the upper curved edge 172B meets the inner arcuate portion 172D at junction 172G while the opposed lower curved edge 172C meets the inner arcuate portion 172D at junction 172H.

FIG. 11A also shows an imaginary x and y-axis coordinate system in dashed lines that is centered on the terminal pin 130A. An imaginary vertical line 182 extending through junctions 172G and 172H intersects the x-axis to the left of the y-axis. With this orientation of the shaped opening 172, the inner arcuate portion 172D is centered along the x-axis at about 9 o'clock with respect to the clock face shown in FIG. 11 and contacts the perimeter of the terminal pin 130A through an arc of about 90° to about 180°. This positioning means that only with respect to opening 172, the polymeric or ceramic washer 170 is capable of lateral movement only in a leftwards direction along the x-axis. Movement to the right along the x-axis is blocked by the inner arcuate portion 172D contacting the terminal pin 130A while movement in an upwardly direction and a downwardly direction along the y-axis is blocked by those portions of the inner arcuate portion 172D that reside immediately adjacent to the junctions 172G and 172H, respectively.

Figure 11B:
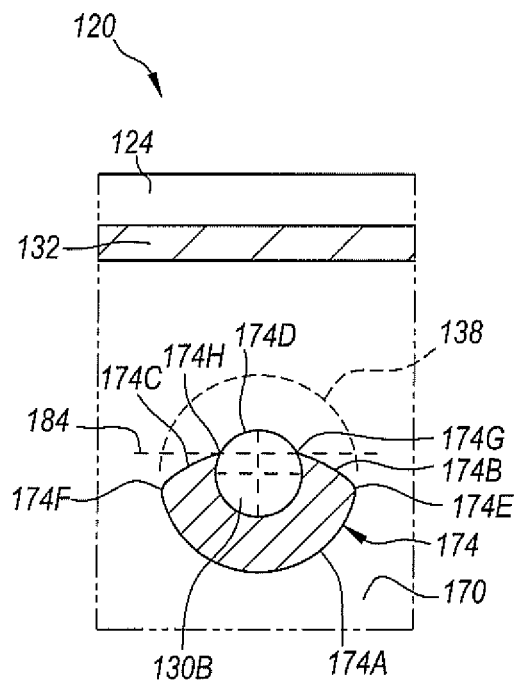

As particularly shown in FIG. 11B, opening 174 associated with terminal pin 130B has a shape that is similar to that of opening 172 about terminal pin 130A, except that its inner arcuate portion contacts the perimeter of the terminal pin 130B centered at about 12-o'clock with respect to the clock face shown in FIG. 11. Opening 174 has an outer perimeter portion 174A that extends from about 90° to about 180° about the circular perimeter of the gold braze 138 that resides underneath the polymeric or ceramic washer 170 at terminal pin 130B. The outer perimeter portion 174A extends to opposed inwardly extending right and left edges 174B and 174C that in turn extend to an inner arcuate portion 174D. The outer perimeter portion 174A meets the right curved edge 174B at junction 174E and the left curved edge 184C at junction 174F. Further, the right curved edge 174B meets the inner arcuate portion 174D at junction 174G while the opposed left curved edge 174C meets the inner arcuate portion 174D at junction 174H.

FIG. 11B also shows an imaginary x-axis and y-axis coordinate system in dashed lines that is centered on the terminal pin 130B. An imaginary horizontal line 184 extending through junctions 174G and 174H intersects the y-axis above the y-axis. With this orientation of the shaped opening 174, the inner arcuate portion 174D is centered along the y-axis at about 12 o'clock with respect to the clock face shown in FIG. 11 and contacts the perimeter of the terminal pin 130B through an arc of about 90° to about 180°. This positioning means that only with respect to opening 174, the polymeric or ceramic washer 170 is capable of lateral movement in only an upwardly direction along the y-axis. Movement in a downwardly direction along the y-axis is blocked by the inner arcuate portion 174D contacting the terminal pin 130B while movement in a rightwards direction and a leftwards direction along the x-axis is blocked by those portions of the inner arcuate portion 174D that reside immediately adjacent to the junctions 174G and 746H, respectively.

Figure 11C:
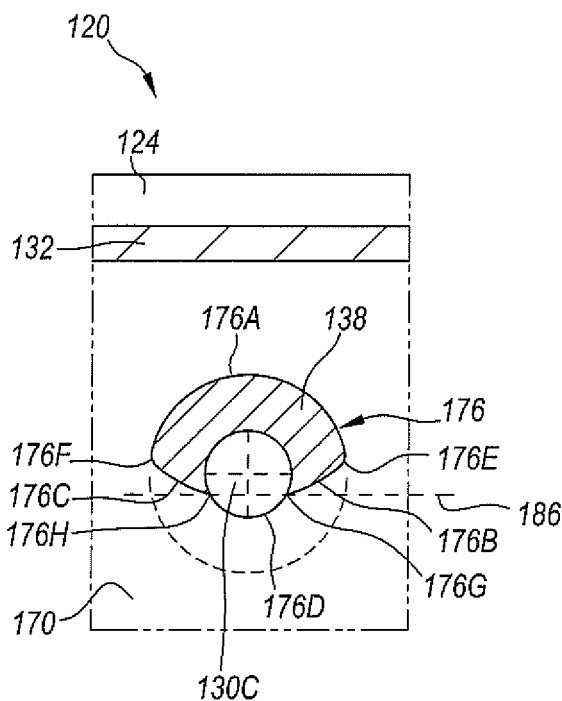

FIG. 11C shows that the opening 176 associated with terminal pin 130C has a shape that is similar to those of openings 172 and 174 about terminal pins 130A and 130B, except that its inner arcuate portion contacts the perimeter of the terminal pin 130C centered at about 6-o'clock with respect to the clock face shown in FIG. 11. Opening 176 has an outer perimeter portion 176A that extends from about 90° to about 180° about the circular perimeter of the gold braze 138 that resides underneath the polymeric or ceramic washer 170 at terminal pin 130C. The outer perimeter portion 176A extends to opposed inwardly extending right and left edges 176B and 176C that in turn meet an inner arcuate portion 176D. The outer perimeter portion 176A meets the right curved edge 176B at junction 176E and the left curved edge 176C at junction 176F. Further, the right curved edge 176B meets the inner arcuate portion 176D at junction 176G while the opposed left curved edge 176C meets the inner arcuate portion 176D at junction 176H.

FIG. 11C also shows an imaginary x-axis and y-axis coordinate system in dashed lines that is centered on the terminal pin 130C. An imaginary horizontal line 186 extending through junctions 176G and 176H intersects the y-axis below the x-axis. With this orientation of the shaped opening 176, the inner arcuate portion 176D is centered along the y-axis at about 6 o'clock with respect to the clock face shown in FIG. 11 and contacts the perimeter of the terminal pin 130C through an arc of about 90° to about 180°. This positioning means that only with respect to opening 176, the polymeric or ceramic washer 176 is capable of movement only in a downwardly direction along the y-axis. Movement in an upwardly direction along the y-axis is blocked by the inner arcuate portion 176D contacting the terminal pin 130C while movement in a rightwards direction and a leftwards direction along the x-axis is blocked by those portions of the inner arcuate portion 130D that reside immediately adjacent to the junctions 176G and 176H, respectively.

Opening 178 has a similar structure and orientation as previously described for opening 174.

Figure 11D:
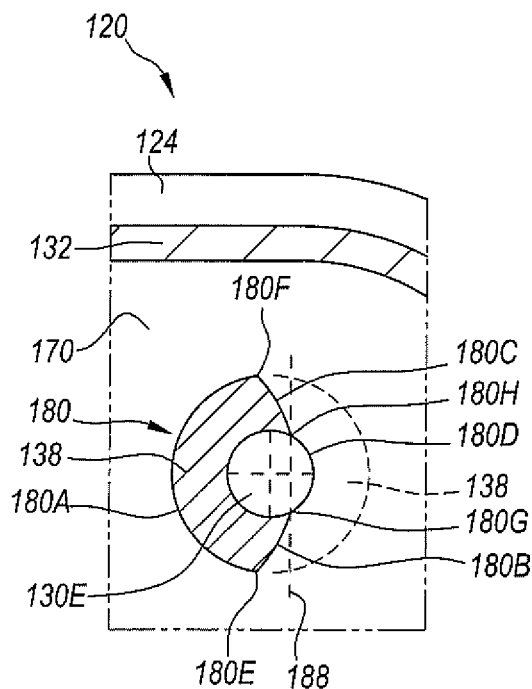
Figure 11E:
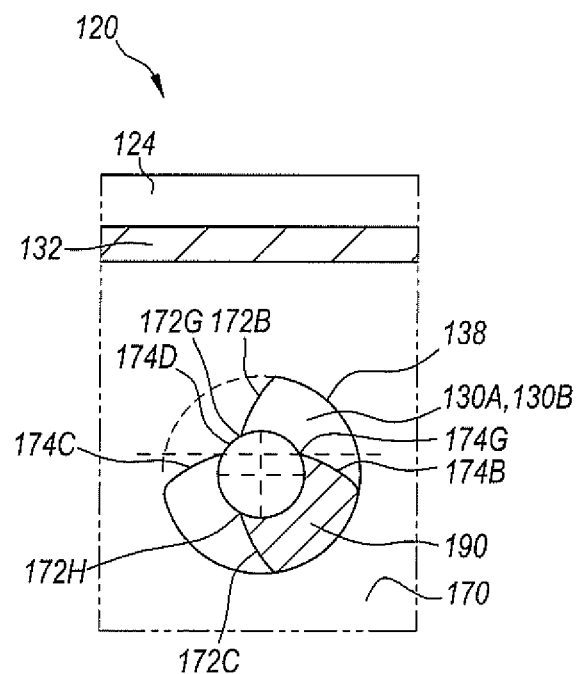
FIG. 11E shows openings 172 and 174 from FIGS. 11A and 11B superimposed one on top of the other.

FIG. 11D shows that the opening 180 associated with terminal pin 130E has a shape that is similar to those of openings 172, 174, 176 and 178 about terminal pin 130A, 130B, 130C and 130D, respectively, except that its inner arcuate portion contacts the perimeter of the terminal pin 130E centered at about 3 o'clock with respect to the clock face shown in FIG. 11. Opening 180 has an outer perimeter portion 180A that extends from about 90° to about 180° about the circular perimeter of the gold braze 138 that resides underneath the polymeric or ceramic washer 170 at terminal pin 130E. The outer perimeter portion 180A extends to opposed inwardly extending right and left edges 180B and 180C that in turn extend to an inner arcuate portion 180D. The outer perimeter portion 180A meets the right curved edge 180B at junction 180E and the left curved edge 180C at junction 180F. Further, the right curved edge 180B meets the inner arcuate portion 180D at junction 180G while the opposed left curved edge 180C meets the inner arcuate portion 180D at junction 180H.

FIG. 11D also shows an imaginary x-axis and y-axis coordinate system in dashed lines that is centered on the terminal pin 130E. An imaginary vertical line 188 extending through junctions 180G and 180H intersects the x-axis to the right of the y-axis. With this orientation of the shaped opening 180, the inner arcuate portion 180D is centered along the x-axis at about 3 o'clock with respect to the clock face shown in FIG. 11 and contacts the perimeter of the terminal pin 130E through an arc of about 90° to about 180°. This positioning means that only with respect to opening 180, the polymeric or ceramic washer 170 is capable of movement only in a rightwards direction along the x-axis. Movement in a leftwards direction along the x-axis is blocked by the inner arcuate portion 180D contacting the terminal pin 130E while movement in an upwards direction and a downwards direction along the y-axis is blocked by those portions of the inner arcuate portion 180D that reside immediately adjacent to the junctions 180G and 180H, respectively.

That way, with respect to an imaginary configuration where at least two of the shaped openings 172, 174 or 178, 176 and 180 are superimposed one on top of the other and with respect to their orientations in the polymeric or ceramic washer 170, if the combined or cumulative arcuate distance measured in degrees of the respective inner arcuate portions 172D, 174D or 178D, 176D and 180D of the at least two shaped openings about a terminal pin, subtracting overlap, results in a gap between the combined inner arcuate portions of the superimposed openings that is less than the diameter of any one of the terminal pins 130A to 130F (assuming equal diameters for the terminal pins 130A to 130F), then the novel self-centering polymeric or ceramic washer 170 illustrated in FIGS. 9 to 11 and 11A to 11D is prevented from any lateral movement in a rightwards, leftwards, upwards, or downwards direction with respect to the feedthrough 120 shown in FIGS. 4 to 6.

For example, FIG. 11E shows openings 172 and 174 superimposed on top of the other. The inner arcuate portion 172D of opening 172 extends from junction 172G to 172H. The inner arcuate portion 174D of opening 174 extends from junction 174G to 176H. As the drawings shows, the remaining portion 190 of one of the terminal pins 130A, 130B that is not contacted by one of the inner arcuate portions 172D and 174D extends from junction 172H of opening 172 to junction 174G of opening 174. A straight line intersecting those junctions 172H, 174G results in a gap that is less than the diameter of the terminal pins 130A and 130B. This means that the polymeric or ceramic washer 170 is prevented from any lateral movement with respect to the device side of the insulator 120. The same applies to terminal pins 130C to 130F (FIG. 6).

If, on the other hand, with respect to an imaginary configuration with at least two of the shaped openings 172, 174 or 178, 176 and 180 being superimposed one on top of the other so that the combined or cumulative arcuate distance measured in degrees of the respective inner arcuate portions 172D, 174D or 178D, 176D and 180D about a terminal pin 130, subtracting overlap, results in a gap between the superimposed openings that is greater than the diameter of at least one of the terminal pins 130A to 130F (assuming equal diameters for the terminal pins 130A to 130F), then a third one of the shaped openings 172, 174 or 178, 176 and 180 is needed. That is with respect to an imaginary configuration where at least three of the shaped openings 172, 174 or 178, 176 and 180 are superimposed one on top of the other and with respect to their orientations in the polymeric or ceramic washer 170 so that the combined or cumulative arcuate distance measured in degrees of the respective inner arcuate portions 172D, 174D or 178D, 176D and 180D about a terminal pin, subtracting overlap, results in a gap between the superimposed openings that is less than the diameter of any one the terminal pins 130A to 130F (assuming equal diameters for the terminal pins 130A to 130F), then the novel self-centering polymeric or ceramic washer 170 illustrated in FIGS. 11, 11A, 11B, 11C and 11D is prevented from any lateral movement in a rightwards, leftwards, upwards, or downwards direction with respect to the feedthrough 120.

Moreover, with respect to an imaginary configuration where there is no configuration with at least three of the shaped openings 172, 174 or 178, 176 and 180 being superimposed one on top of the other and with respect to their orientations in the washer 170 so that the combined or cumulative arcuate distance measured in degrees of the respective inner arcuate portions 172D, 174D or 178D, 176D and 180D about a terminal pin, subtracting overlap, results in a gap between the superimposed openings that is greater than the diameter of at least one of the terminal pins 130A to 130F (assuming equal diameters for the terminal pins 130A to 130F), then a fourth one of the shaped openings 172, 174 or 178, 176 and 180 is needed. That is with respect to an imaginary configuration where at least four of the shaped openings 172, 174 or 178, 176 and 180 are superimposed one on top of the other and with respect to their orientations in the polymeric or ceramic washer 170 so that the combined or cumulative arcuate distance measured in degrees of the respective inner arcuate portions 172D, 174D or 178D, 176D and 180D about a terminal pin 130, subtracting overlap, results in a gap between the superimposed openings that is less than the diameter of any one the terminal pins 130A to 130F (assuming equal diameters for the terminal pins 130A to 130F), then the self-centering polymeric or ceramic washer 170 illustrated in FIGS. 11, 11A, 11B, 11C and 11D is prevented from any lateral movement in a rightwards, leftwards, upwards, or downwards direction with respect to the feedthrough 120.

Thus, it is within the scope of the present invention that in order to prevent lateral movement of the self-centering polymeric or ceramic washer 170 in a rightwards, leftwards, upwards, or downwards direction with respect to the planar faces of the insulator and ferrule device sides of the feedthrough 120 shown in FIGS. 3 to 6, at least two of the shaped openings 172, 174 or 178, 176 and 180 are required. That is with respect to the orientations of the shaped openings 172, 174 or 178, 176 and 180 in the polymeric or ceramic washer 170 being superimposed one on top of the other in an imaginary configuration so that the combined or cumulative arcuate distance measured in degrees of the respective inner arcuate portions 172D, 174D or 178D, 176D and 180D about a terminal pin 130, subtracting overlap, results in a gap between the superimposed openings that is less than the diameter of at least one of the terminal pins 130A to 130F (assuming equal diameters for the terminal pins 130A to 130F). That way, the novel polymeric or ceramic washer 170 of the present invention resolves the washer mis-location or misalignment issues of the prior art polymeric washer 152 illustrated in FIG. 7.

Referring once again to FIG. 11, the outer perimeter portions 172A, 174A, 176A, 178A and 180A of the shaped openings 172, 174, 176, 178 and 180 for the polymeric or ceramic washer 170 selectively expose the terminal pin-to-insulator gold brazes 138 at the respective terminal pins 130A to 130F. The exposed portions of the gold braze 138 allow for robust and reliable oxide-resistant electrical connections to an EMI filter capacitor 122 (FIGS. 3 and 4), an EMI filter capacitor 158 (FIG. 5) or an EMI filter circuit board 200 (FIG. 6). Even though the gold brazes 138, which hermetically seal the terminal pins 130A to 130F to the feedthrough insulator 126 are partially covered by the respective polymeric or ceramic washer openings 172, 174, 176, 178 and 180, there is enough exposed gold for a low resistance, low impedance electrical connection.

In order for there to be a sufficient high-voltage stand-off distance, a keep-out zone 192 as the distance between the inner edge of the gold braze 132 sealing the insulator 126 to the ferrule 124 and the closest edge of one of the adjacent openings 172, 174, 176, 178 and 180 is illustrated in FIG. 11. For example, the polymeric or ceramic washer-shaped opening orientation of the five pole in-line terminal pins 130A to 130E of FIG. 11 can be a challenge for providing sufficient stand-off distance. In high-voltage AIMDs, such as an ICD, or when low voltage AIMDs are exposed to defibrillation paddles or an automatic external defibrillator (AED), the high-voltage keep-out zone 192 becomes very important. It is a well-known principle in high-voltage engineering that any sharp point tends to be an equipotential field-line stress concentrator. In fact, a needlepoint-shaped corner is actually one of the worst cases for high-voltage breakdown of air or insulation between conductors. In that respect, the sharper the corner, the greater the threat of dielectric breakdown.

For example, with reference to terminal pins 130A, 130C and 130E shown in FIG. 11, the junction 172E where the outer perimeter portion 172A meets the upper curved edge 172B of shaped opening 172 is shown having a relatively sharp point that is oriented at about 12 o'clock and pointed directly into the high-voltage keep-out zone 192. Similarly, the outer perimeter portion 180A of shaped opening 180 meets the left curved edge 180C at junction 180F, which is shown as a relatively sharp junction. While these junctions 172E and 180F are shown as being relatively sharp only for the sake of illustration, they illustrate that a relatively high volts per mil (V/mil) stress may occur where they exist. On the other hand, the shaped opening 176 about terminal pin 130C has its outer perimeter portion 176A having a relatively large radial contour. The large radial contour of the outer perimeter portion 176A faces the gold braze 132, which is also at the edge of the high-voltage keep-out zone 192. Comparing the sharp corners 172E, 180F of the shaped openings 172, 180 about the respective terminal pins 130A and 130E with respect to the large radial contour 176A of the shaped opening 176 about terminal pin 130C, it is apparent that the latter design reduces the V/mil stress and is therefore unlikely to exhibit high-voltage breakdown than the sharp corners 172E, 180F at terminal pins 130A, 130E. Dielectric breakdown can lead to catastrophic high-voltage avalanche. That is the case even though the exposed gold braze portions 138 of the terminal pins 130A and 130E have a keep-out zone 192 with respect to the insulator-to-ferrule braze 132 of the same distance as that for terminal pin 130C.

Figure 12:
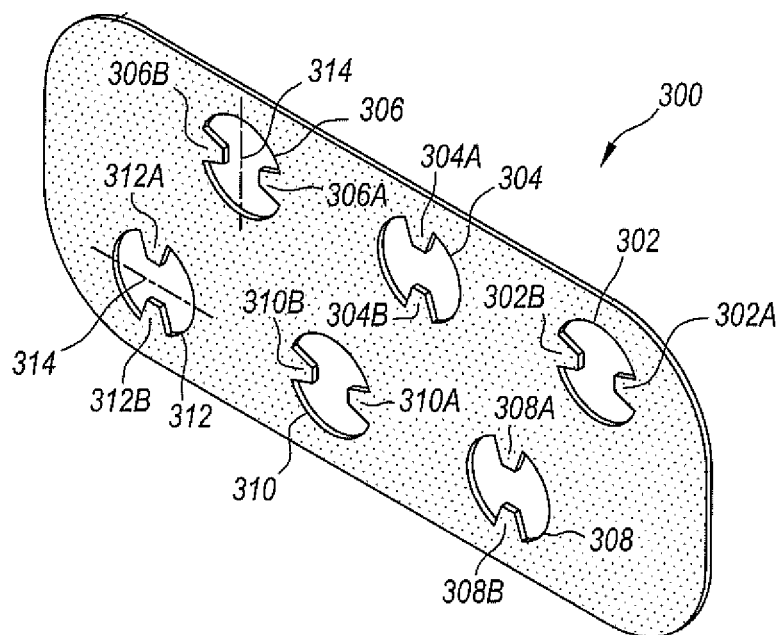
FIG. 12 an isometric view of another embodiment of a novel self-centering polymeric or ceramic washer 300 that has shaped openings with two diametrically opposed inwardly extending tooth-like structures providing opposed inner arcuate portions according to the present invention.

FIG. 12 is an isometric view of another embodiment of a novel self-centering polymeric or ceramic washer 300 according to the present invention. The self-centering polymeric or ceramic washer 300 has uniquely shaped openings 302 to 312 that each have two diametrically opposed tooth-like structures or inwardly extending projections that provide opposed inner arcuate portions. In particular, opening 302 has opposed tooth-like projections 302A and 302B, opening 304 has tooth-like projections 304A, 304B, opening 306 has tooth-like projections 306A, 306B, opening 308 has tooth-like projections 308A, 308B, opening 310 has tooth-like projections 310A, 310B, and opening 312 has tooth-like projections 312A, 312B. The openings are oriented so that an imaginary line 314 centered between the tooth-like projections is aligned at 12 o'clock to 6 o'clock for openings 302, 306 and 310, and an imaginary line 316 that is centered between the tooth-like projections for openings 304, 308 and 314 is aligned at 3 o'clock to 9 o'clock. The openings being aligned from 12 o'clock to 6 o'clock and from 3 o'clock to 9 o'clock are in an alternating sequence.

When the polymeric or ceramic washer 300 is seated on top of a hermetically sealed feedthrough, for example the feedthrough 120 shown in FIGS. 3 to 6, it is within the scope of the present invention that the inner arcuate portions of the tooth-like projections of each of the openings 302 to 312 are configured to contact a terminal pin. Then, if both of the spaced apart gaps between the opposed inner arcuate portions contacting a terminal pin are less than the diameter of the terminal pin, the washer 300 is prevented from any lateral movement with respect to the device side of the insulator 126 for the feedthrough 120.

Figure 13:
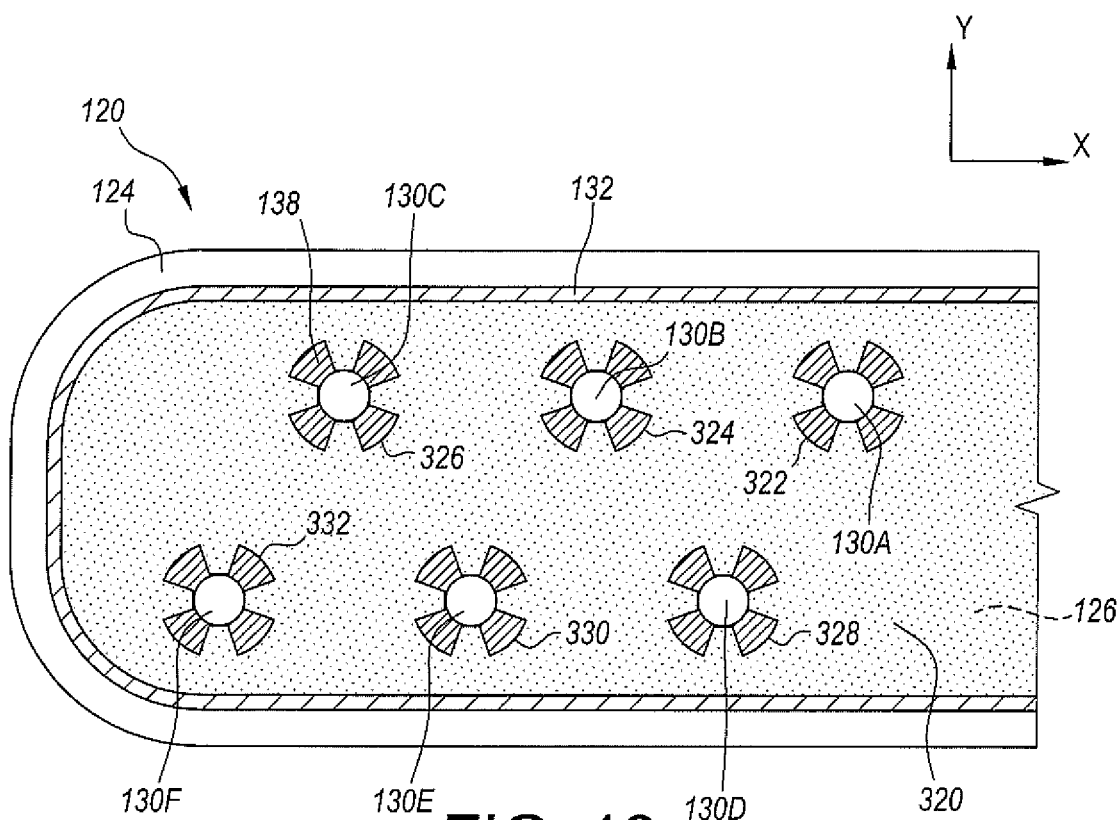
FIG. 13 is a plan view of a hermetically sealed feedthrough 120 on which a novel self-centering polymeric or ceramic washer 320 having shaped openings with four inwardly extending tooth-like structures providing four inner arcuate portions according to the present invention.

FIG. 13 illustrates another embodiment of a self-centering polymeric or ceramic washer 320 according to the present invention. The polymeric or ceramic washer 320 is positioned on the insulator 126 for a hermetically sealed feedthrough 120 (FIGS. 3 to 6). The self-centering polymeric or ceramic washer 320 is similar to the self-centering washer 300 shown in FIG. 12, except that each of the shaped openings 322, 324, 326, 328, 330 and 332 comprises four internal tooth-like structures (instead of two) that contact respective feedthrough terminal pins 130A to 130F. The four tooth-like structures provide four inner arcuate portions that fixedly align the polymeric or ceramic washer 320 about the terminal pins 130A to 130F. In that respect, the self-centering washer 320 does not require a unique orientation when mounted on the feedthrough 120. The four tooth-like structures for each opening, being symmetric, prevent inadvertent lateral misalignment of the washer 320 with respect to the device side of the insulator 126 for the feedthrough 120.

Figure 14:
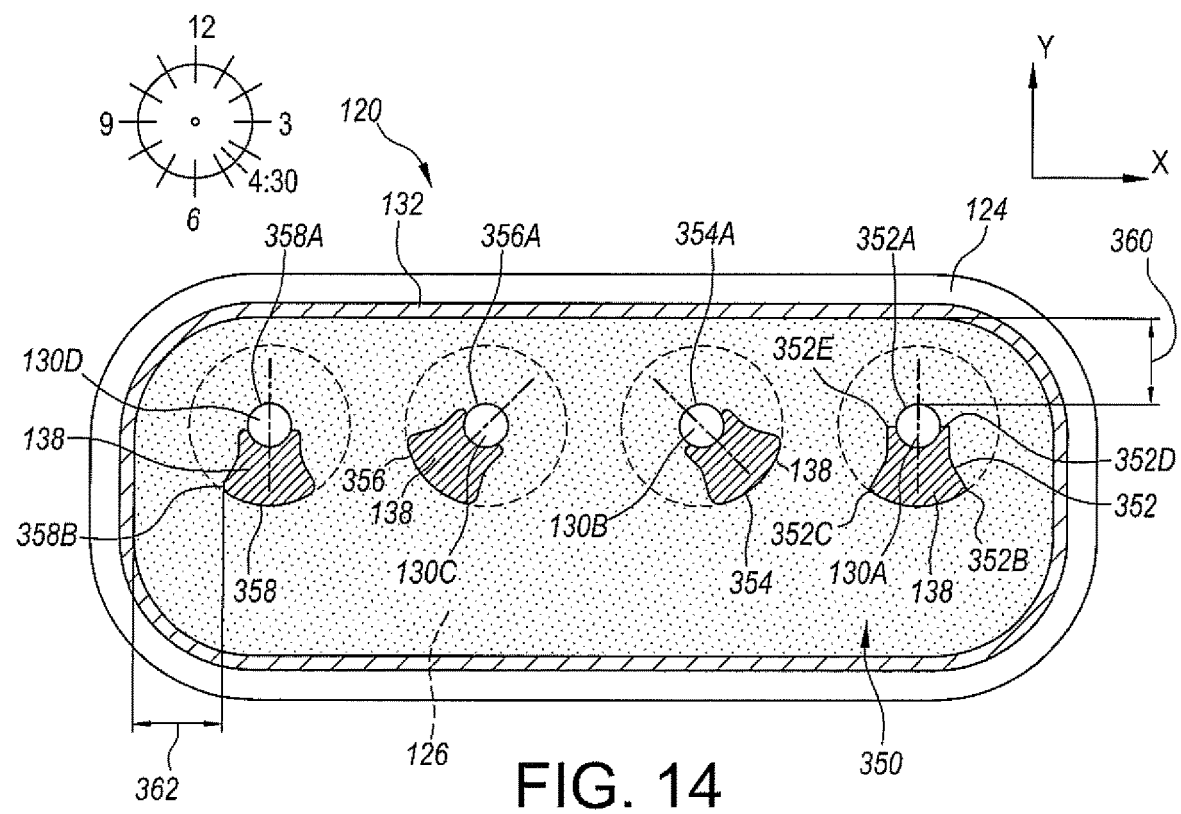
FIG. 14 is a plan view of a hermetically sealed feedthrough 120 on which a self-centering polymeric or ceramic washer 350 is desirably located so that the exposed insulator-to-terminal pin gold brazes 138 are outside of high-voltage keep-out zones 360 and 362.

FIG. 14 is a plan view of another embodiment of a self-centering polymeric or ceramic washer 350 having a number of spaced-apart novel baseball playing field-shaped openings 352, 354, 356 and 358. The washer 350 is positioned on top of the insulator 126 for the hermetically sealed feedthrough 120. In this embodiment, each baseball playing field-shaped opening 352, 354, 356 and 358 is oriented so that none of the exposed terminal pin-to-insulator gold brazes 138 encroach into the increased distance keep-out zone 360 (i.e., none of these gold brazes 138 extend into the high-voltage keep-out zone 360). In particular, the open portion of the gold braze adjacent to terminal pin 130A is generally oriented at 6 o'clock, the open portion of the gold braze adjacent to terminal pin 130B is oriented at 4:30 o'clock, the open portion of the gold braze adjacent to terminal pin 130C is oriented at 7:30 o'clock, and the open portion of the gold braze adjacent to terminal pin 130D is oriented at 6 o'clock.

The increased keep-out zone 360 distance extends ideally to the external surface of each terminal pin 130A to 130D and to the insulator-to-ferrule gold braze 132, thereby providing optimal high-voltage stand-off distance therebetween. Optimal high-voltage stand-off distance greatly improves insulative reliability by providing increased safety margins against high-voltage insults. Each shaped opening 352, 354, 356 and 358 of the self-centering polymeric or ceramic washer 350 has a baseball playing field-shaped opening that has a minor arc 352A, 354A, 356A and 358A abutting its corresponding terminal pin 130A to 130D. At least two shaped openings must be selectively oriented to prevent the self-centering polymeric or ceramic washer 350 from undesirably moving in any lateral direction along the planar faces of the insulator 126 of the feedthrough 120. As previously disclosed, EMI filter capacitor 122 or EMI filter circuit board 200 electrical connection to the exposed gold brazes 138 is important in order to provide oxide-resistant, low impedance, low resistance active terminal pin electrical connections.

Referring again to FIG. 14, on the left side, another high-voltage keep-out zone 362 is illustrated. This keep-out zone 362 extends to the rounded corner 358B of opening 358 at the exposed gold braze 138 and to the insulator-to-ferrule gold braze 132. As disclosed earlier, an exposed gold braze 138 at rounded corner 358B is preferred compared to the exemplary sharp corners 352B, 352C, 352D and 352E of opening 352 adjacent to terminal pin 130A.

Figure 15:
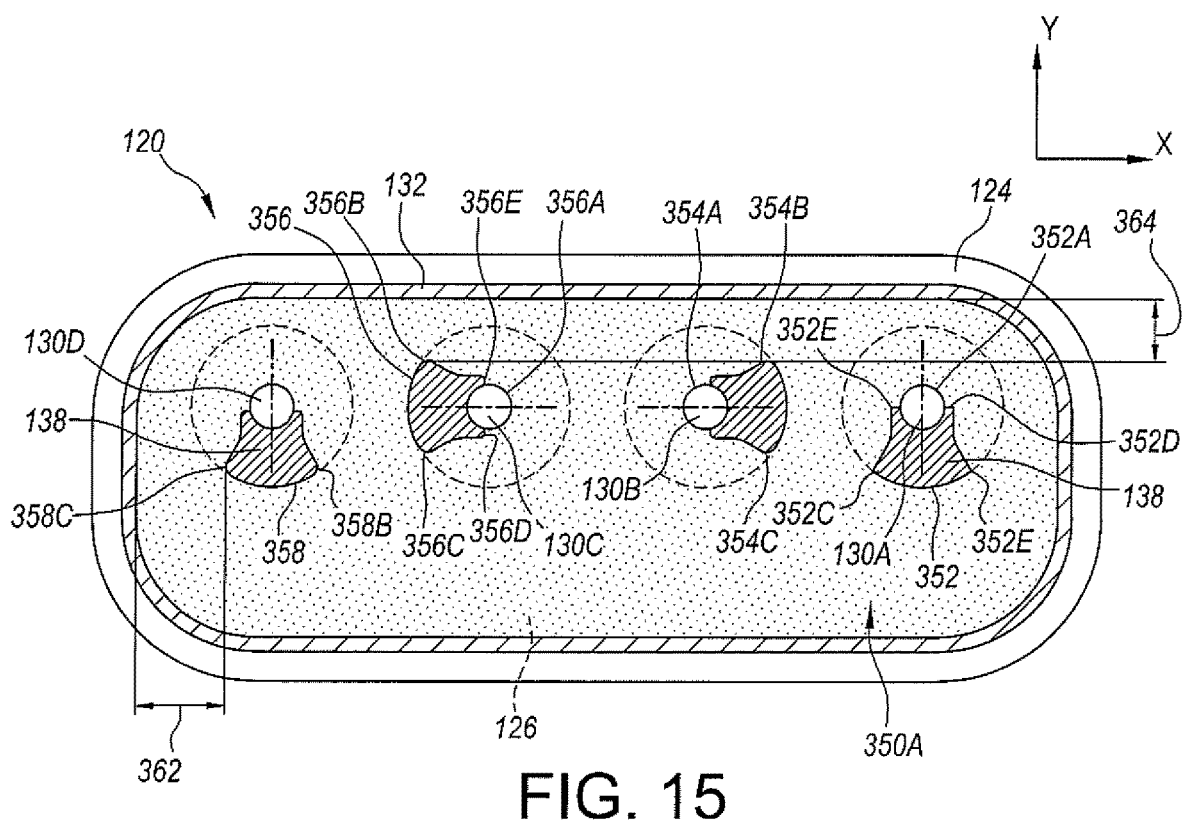
FIG. 15 is a plan view of a hermetically sealed feedthrough 120 on which a self-centering polymeric or ceramic washer 350A with terminal pins 130A to 130D received in baseball playing field-shaped openings for so that the exposed insulator to terminal pin gold brazes 138 are outside a narrower high-voltage keep-out zone 364 as compared to the embodiment shown in FIG. 15.
Figure 16:
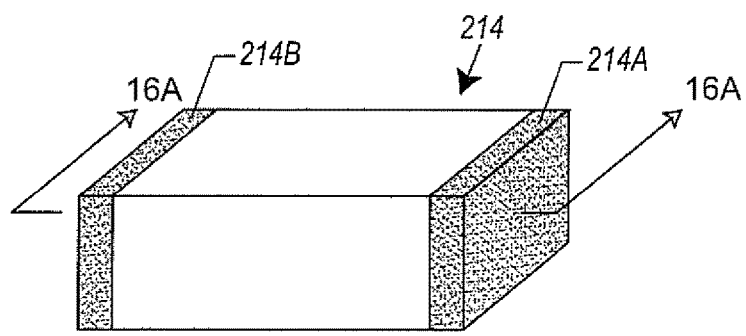
FIG. 16 is a perspective view of the MLCC chip capacitor 214 as a representative one of the chip capacitors mounted on the circuit board 200 shown in FIG. 6.
Figure 16A:
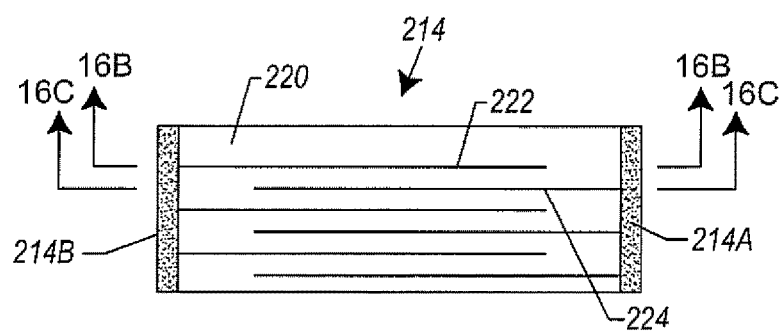
FIG. 16A is a cross-sectional view taken along line 16A-16A of FIG. 16.
Figure 16B:
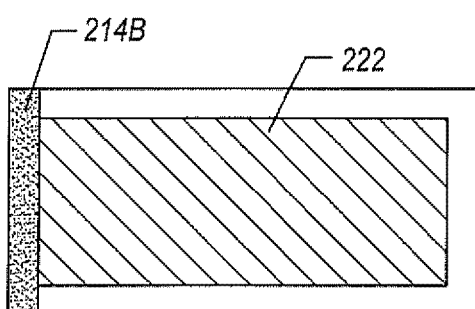
FIG. 16B is a cross-sectional view taken along line 16B-16B of FIG. 16A.
Figure 16C:
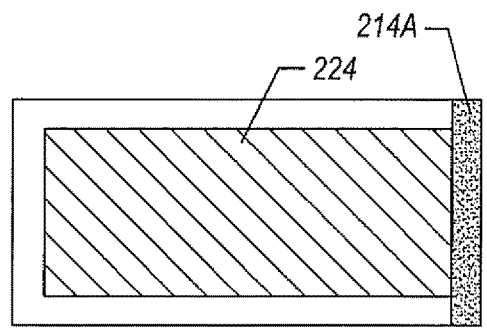
FIG. 16C is a cross-sectional view taken along line 16C-16C of FIG. 16A.

FIG. 15 illustrates another embodiment of the self-centering polymeric or ceramic washer 350A shown in FIG. 14, except that the open portion of the gold braze adjacent to terminal pin 130B is oriented at 3 o'clock, and the open portion of the gold braze adjacent to terminal pin 130D is oriented at 6 o'clock. As can be seen, the clocking-wise extent illustrated in this embodiment prevents inadvertent movement of the polymeric or ceramic washer 350A in any lateral direction along the planar faces of the insulator 126 and ferrule device sides of the feedthrough 120.

The clock-wise orientations shown in FIG. 15, however, position the exposed gold brazes 138 at a narrower keep-out zone 364 in comparison to the wider keep-out zone 360 illustrated in FIG. 14. The keep-out zone 364 shown in FIG. 15, while reduced, is not reduced as much as, for example, the keep-out zone 192 shown in the polymeric or ceramic washer 170 illustrated in FIG. 11 (distance 192 is less than HV stand-off distance 364). Corners 354B, 354C, 354D, 354E, 356B, 356C, 356D, 356E, 358B, 358C, 358D and 358E are radiused which helps reduce volts/mil stress. That is in contrast to the sharp-edged corners 352B, 352C, 352D and 352E for shaped opening 352, which are undesirable.

Referring again to FIG. 15, one also has to be concerned about the keep-out zone 362, which has been previously discussed. In this case, keep-out zone 362 is adjacent to rounded corner 358C of shaped opening at terminal pin 130D. The rounded corner 358C in comparison to the sharp corners 352B, 352C, 352D and 352E is preferred. That is because the rounded corners have reduced volts/mil stress.

Figure 19A:
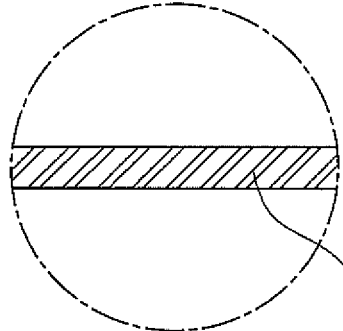
FIG. 19A is an elevational view illustrating the novel self-centering washer 170 shown in FIGS. 6, 6A, 6B, 9 to 11 and 11A to 11E and the self-centering washers 300, 320, 350 and 350A shown in respective FIGS. 12 to 15 comprising a polymeric or ceramic material.

Referring now to FIG. 19A, this drawing shows an elevational view illustrating the novel self-centering polymeric or ceramic washer 170 shown in FIGS. 6, 6A, 6B, 9 to 11 and 11A to 11E and the self-centering polymeric or ceramic washers 300, 320, 350 and 350A shown in respective FIGS. 12 to 15 comprising a homogeneous thermoplastic or ceramic. If polymeric, the washers 300, 320, 350 and 350A may be made using conventional punch and cut methods from a flexible or semi-rigid film, tape, or equivalent insulating material (low plasticity, high elasticity), or they may be made from a nearly rigid polymeric or ceramic material.

Suitable polymeric materials for the washers 170, 300, 320, 350 and 350A include polyimide (for example, Kapton®), aromatic, semi-aromatic, aliphatic, partially fluorinated aliphatic, acrylates, epoxies, elastomers, phenolics, polyimides, polyolephins, and fluoropolymers. Other suitable polymeric materials include silicone, polyurethane, polyester, polyethylene, polypropylene, polyamide (including synthetic polyamide, also known as nylon), acrylic, polyacrylates, and combinations thereof. Additional electrically insulative materials that are suitable for the washers 170, 300, 320, 350 and 350A include flowable perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl copolymers including ethylene-vinyl acetate (EVA) or polyethylene-vinyl acetate (PEVA), polytetrafluoroethylene, ethylene tetrafluoroethylene, polyetherimide, acetal, polyacetal, polyformaldehyde, phenolic, polysulfide, and combinations thereof. Kapton® is a registered trademark of DuPont for polyimide films used as substrates for flexible printed circuits.

Suitable ceramic materials for the washers 170, 300, 320, 350 and 350A are selected from $Al_2O_3$, Bao, Cao, $CeO_2$, MgO, $ZrO_2$, $SiO_2$, $TiO_2$, $Al_2SiO_{53}$, $BaTiO_3$, $SrTiO_2$, ZnO, $Si_3N_4$, AlN, BN and combinations thereof. Various stabilized or partially stabilized zirconia may also be used including zirconia toughened alumina (ZTA) and alumina toughened zirconia (ATZ), yttrium stabilized zirconia (YSZ), yttrium-toughened zirconia (YTZP), and combinations thereof. Some nitrides may also be used, such as, aluminum nitride (AN), silicon nitride ($Si_3N_4$), boron nitride (BN), carbon nitride (CN) and combinations thereof. Alumina ($Al_2O_3$) is a preferred material for the washers 170, 300, 320, 350 and 350A.

Figure 19B:
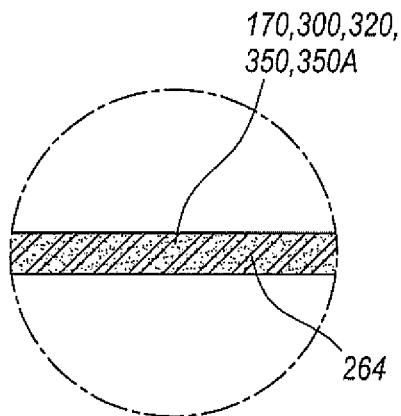
FIG. 19B is an elevational view illustrating an embodiment of the self-centering polymeric washers 170, 300, 320, 350 and 350A shown in FIG. 19A containing insulating nanoparticles.

FIG. 19B is an elevational view illustrating an embodiment of the self-centering polymeric washers 170, 300, 320, 350 and 350A shown in FIG. 19A but containing insulating nanoparticles 264. The insulating nanoparticles 264 may be polymeric, ceramic or combinations thereof. Polymeric nanoparticle 264 may be selected from any of the insulating materials listed above for use as the polymeric washers 170, 300, 320, 350 and 350A.

Ceramic nanoparticles 264 may be selected from alumina, baria, calcia, ceria, magnesia, silica, strontia, titania, zirconia ceramic families and combinations thereof. Non-limiting examples of suitable nanoscale metal oxides that can also be used include $Al_2O_3$, Bao, Cao, $CeO_2$, MgO, $ZrO_2$, $SiO_2$, $TiO_2$, $Al_2SiO_{53}$, $BaTiO_3$, $SrTiO_2$, ZnO, $Si_3N_4$, AlN, BN and combinations thereof. Various stabilized or partially stabilized zirconia may also be used including zirconia toughened alumina (ZTA) and alumina toughened zirconia (ATZ), yttrium stabilized zirconia (YSZ), yttrium-toughened zirconia (YTZP), and combinations thereof. Some nitrides may also be used, such as, aluminum nitride (AlN), silicon nitride ($Si_3N_4$), boron nitride (BN), carbon nitride (CN) and combinations thereof.

The nanoparticles 264 may be configured as particulates, short fibers, long fibers, spheres, flakes, submicron fibers, which are isotropically dispersed within the base polymeric material. It is understood that the nanoparticles 264 may be of the same material, or, alternatively, they may be a combination of one or more of the suitable materials listed above. For example, a combination of various nanoparticles 264 may be used. Insulating nanoparticle 264 material selection is defined by the specific electrical performance needs of an application and the physical, chemical, and electrical properties of the nanoparticle material. The above nanoparticles and particle configurations are applicable to all polymeric washer embodiments disclosed herein.

The insulative nanoparticles 264 are represented by small uniform dots in FIG. 19B that are evenly distributed throughout the various polymeric washers 170, 300, 320, 350 and 350A. While small dots are used to indicate the nanoparticles 264, in reality, the nanoparticles 264 are so small that they are not visible to the naked eye (requires microscopy techniques). The small dots are intended to distinguish the embodiments having nanoparticles according to the present invention from those embodiments that do not.

Regarding particle size, the nanoparticles 264 range from greater than 0 nanometers to about 40,000 nanometers. As such, the nanoparticles 264 can range from greater than 0 nanometers to about 100 nanometers, which is the common industry range for the term "nano". The particle size range of the nanoparticles 264, however, also includes fine and micron-sized particles ranging from greater than about 100 nanometers (0.1 microns) to about 40,000 nanometers (40 microns).

If the self-centering washers 170, 300, 320, 350 and 350A are made of ceramic, there is any need for there to be added nanoparticles. Ceramic materials, for example, the preferred ceramic alumina, are inherently highly insulative.

Figure 19C:
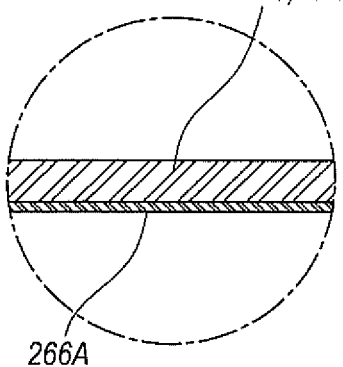
FIG. 19C is an elevational view illustrating the self-centering polymeric or ceramic washers 170, 300, 320, 350 and 350A shown in FIG. 19A having an adhesive 266A disposed on only one surface of the washer.
Figure 19D:
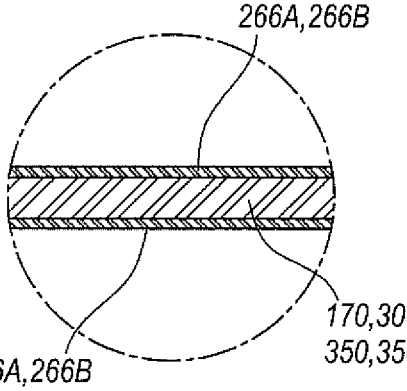
FIG. 19D is an elevational view illustrating the self-centering polymeric or ceramic washers 170, 300, 320, 350 and 350A shown in FIG. 19A having either an adhesive 266A or a thermoplastic material 266B disposed on both surfaces of the washer.

As further shown in FIGS. 19C and 19D, the polymeric or ceramic washers 170, 300, 320, 350 and 350A may be a single or double-sided adhesive-backed 266A washer or a thermoplastic-backed 266B washer. Suitable adhesives 266A include reactive, non-reactive, pressure-sensitive, a synthetic or natural adhesives selected from acrylics, acrylates, acrylonitrites, cyanoacrylates, polyurethanes, polyvinyl acetates, polyvinyl alcohols, polyvinyl chlorides, polyesters, phenol-formaldehydes, polyamides, polyethylenes, polypropylenes, polysulfides, polyvinyl pyrrolidones, epoxies, styrene-butadienes, styrene acrylic copolymerics, silicones, silyl modified polymerics, among others. The adhesive 266A may also include biocompatible, biostable, and non-toxic materials in the family of polyimides, polyamides, polyethylene terephthalates (PET), polydimethylsiloxane (PDMS), polytetrafluoroethylene (PTFE), ethylene tetrafluoroethylene (ETFE), parylenes, polyether block amides (PEBAX), polyetheretherketones (PEEK), polystyrenes, polysulfones, polypropylenes, polycarbonates, polyvinyl chlorides (PVC), polyxylylene polymerics, silicones, including medical-grade adhesives and epoxies.

Suitable thermoplastic materials include a thermoplastic polyurethane, an aliphatic polyester-based thermoplastic polyurethane, an aliphatic and aromatic polycarbonate-based thermoplastic polyurethane, an aromatic polyether-based thermoplastic polyurethane. The term "thermoplastic" refers to any plastic or polymeric material that becomes pliable or moldable at a certain elevated temperature and solidifies on cooling. Thermoplastic or polymeric materials may be transformed into thermosetting plastic and polymeric materials by free radical cross-linking using techniques, such as, but not limited to, redox initiators or high energy radiation.

Figure 19E:
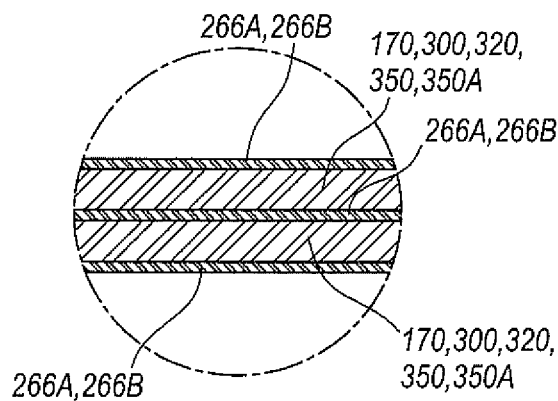
FIG. 19E is an elevational view illustrating two of the self-centering polymeric or ceramic washers 170, 300, 320, 350 and 350A shown in FIG. 19A secured together by an intermediate adhesive 266A or thermoplastic layer 266B and being coated on their respective outer surfaces with an adhesive 266A or thermoplastic material 266B.

Now looking at FIG. 19E, a laminated configuration of two polymeric or ceramic washers is shown. The washers are separated by an adhesive layer 266A or a thermoplastic layer 266B. There is also an adhesive layer 266A or a thermoplastic layer 266B on the outer surfaces of the laminated washer. Importantly, in a laminated configuration, there must not be any separation, delamination, disconnection, disjunction, holes, openings, breaks, cavities, spaces, gas bubbles, or interruptions between the spaced-apart washers that could be a gas gap between the feedthrough insulator 126 and the EMI filter capacitors (FIGS. 3 to 5) or the circuit board 200 (FIG. 6). Proper bonding of the polymeric washers is therefore very important. Adjunct adhesives, epoxies, or polyimides (not shown) can facilitate and improve such bonding. Adding the previously described nanoparticles 264 to the polymeric washers can significantly increase the dielectric breakdown strength of the washer to greater than about 5 to about 10 thousand volts per mil thickness.

In a preferred embodiment, the polymeric washers 170, 300, 320, 350 and 350A of the present invention have a CTE of approximately $8\times10^{-6}/°$ C. at temperatures between 50° C. to 150° C. The CTE of the polymeric washers ranges from about $\geq 6\times10^{-6}/°$ C. to $\leq 12\times10^{-6}/°$ C. An embodiment of the present invention comprises a polyimide washer having a high temperature stability (glass transition temperature of approximately 300° C.) and a ring molecule to absorb mechanical and thermal stresses. The ability to withstand mechanical and thermal stresses is important for both thermal shock and piezoelectric stress induced purposes in ceramic filter capacitors during fast risetime ICD pulses.

Thus, the present invention describes several embodiments of self-centering polymeric or ceramic washers that are configured to be positioned between the insulator of a feedthrough and either an EMI filter capacitor or a circuit board supporting a plurality of EMI filter capacitors. The washers are received over the terminal pins of the feedthrough and have self-centering structures that prevent them from inadvertent lateral movement on the insulator with respect to the terminal pins. One particularly preferred embodiment of a self-centering polymeric or ceramic washer according to the present invention has at least a first shaped opening and a second shaped opening through which first and second terminal pins extend. The first and second shaped openings each have an inner arcuate or curved portion that contacts the respective terminal pin and an outer perimeter portion that exposes the braze sealing the terminal pin to the feedthrough insulator. In an imaginary configuration with the first and second shaped openings superimposed one on top of the other, the cumulative arcuate distance measured in degrees of the inner arcuate portions about one of the terminal pins, subtracting overlap, results in a gap between the superimposed shaped openings that is less than a diameter of either of the first and second terminal pins so that the self-centering polymeric or ceramic washer is prevented from lateral movement along the planar face of the feedthrough insulator.

It is appreciated that various modifications to the inventive concepts described herein may be apparent to those skilled in the art without departing from the spirit and scope of the present invention as defined by the hereinafter appended claims.

What is claimed is:

1. An assembly that is attachable to an active medical device (AMD), the assembly comprising:
   a) a feedthrough, comprising:
      i) an electrically conductive ferrule comprising a ferrule sidewall defining a ferrule opening extending to a ferrule body fluid side spaced from a ferrule device side;
      ii) an insulator hermetically sealed to the ferrule in the ferrule opening by a gold braze, the insulator extending to an insulator body fluid side spaced from an insulator device side, wherein, when the ferrule hermetically sealed to the insulator is attached to an opening in a housing of an AMD, the ferrule body fluid side adjacent to the insulator body fluid side, and the ferrule device side adjacent to the insulator device side reside outside and inside the AMD, respectively; and
      iii) a first terminal pin hermetically sealed to the insulator in a first via hole by a first terminal pin braze, and a second terminal pin hermetically sealed to the insulator in a second via hole by a second terminal pin braze, wherein the first and second terminal pins extend outwardly beyond the insulator device side; and
   b) a circuit board comprising spaced apart circuit board first and second sides, the circuit board supporting at least one circuit board ground plate, wherein the circuit board comprises circuit board first and second active via holes conductively isolated from the circuit board ground plate, and wherein the circuit board further comprises circuit board first and second ground via holes and either a circuit board third ground via hole or a circuit board ground termination conductively connected to the circuit board ground plate;
   c) a polymeric washer positioned between the circuit board first side and the insulator second end surface, the polymeric washer comprising at least a washer first opening and a washer second opening with the first and second terminal pins extending through the respective washer first and second openings and into the circuit board first and second active via holes;
   d) at least a first filter capacitor and a second filter capacitor proximate the circuit board second side, the first filter capacitor comprising first filter capacitor active and ground terminations, and the second filter capacitor comprising second filter capacitor active and ground terminations, wherein the first and second filter capacitor active terminations are electrically connected to the respective first and second terminal pins extending into the circuit board first and second active via holes, and wherein the first and second filter capacitor ground terminations are electrically connected to the at least one circuit board ground plate through the respective circuit board first and second ground via holes; and
   e) an electrical connection material connecting either the circuit board third ground via hole or the circuit board edge termination to a system ground.

2. The assembly of claim 1, wherein:
   a) the washer first opening comprises a washer first opening inner arcuate portion that contacts the first terminal pin and a washer first opening outer perimeter portion that is spaced from the first terminal pin and that exposes a portion of the first terminal pin braze hermetically sealing the first terminal pin to the insulator in the first via hole; and
   b) the washer second opening comprises a washer second opening inner arcuate portion that contacts the second terminal pin and a washer second opening outer perimeter portion that is spaced from the second terminal pin and that exposes a portion of the second terminal pin braze hermetically sealing the second terminal pin to the insulator in the second via hole,
   c) wherein, in an imaginary configuration having the washer first and second openings superimposed one on top of the other and when measured with respect to their orientations in the polymeric washer, the cumulative arcuate distance of the respective washer first and second opening inner arcuate portions about one of the first and second terminal pins, subtracting overlap, results in a gap between the superimposed washer first and second opening inner arcuate portions that is less than a diameter of either of the first and second terminal pins so that the polymeric washer is prevented from lateral movement with respect to the insulator device side.

3. The assembly of claim 1, wherein the washer first and second inner arcuate portions of the respective washer first and second openings each extend about 90° to about 180° around the respective first and second terminal pins.

4. The assembly of claim 1, wherein the washer first and second outer peripheral portions of the respective washer first and second openings each extend about 90° to about 180° around the respective first and second brazes.

5. The assembly of claim 1, wherein the washer first opening outer peripheral portion extends around at least a portion of the perimeter of the first braze.

6. The assembly of claim 1, wherein the washer first opening inner arcuate portion extends to opposed inner arcuate portion first and third ends and the washer first opening outer peripheral portion extends to opposed outer perimeter portion second and fourth ends, and wherein a first curved edge of the washer first opening meets the first and second ends of the respective inner arcuate and outer perimeter portions at first and second rounded junctions, and wherein a second curved edge of the washer first opening meets the third and fourth ends of the respective inner arcuate and outer perimeter portions at third and fourth rounded junctions.

7. The assembly of claim 1, wherein the polymeric washer is selected from silicone, polyurethane, polyester, polyethylene, polypropylene, polyamide, acrylic, polyacrylates, flowable perfluoroalkoxy (PFA), fluorinated ethylene-propylene (FEP), polyetheretherketone (PEEK), polyamide imide (PAI), polyphenyl sulfone (PPSU), polyetherimide (PEI), polymethyl methacrylate (PMMA), acrylonitrile butadiene styrene (ABS), polycarbonate (PC), polyoxymethylene (POM), polystyrene (PS), thermoplastic elastomer (TPE), polyethylene terephthalate (PET), ethylene-vinyl acetate (EVA), polyethylene-vinyl acetate (PEVA), polytetrafluoroethylene, ethylene tetrafluoroethylene, polyetherimide, acetal, polyacetal, polyformaldehyde, phenolic, polysulfide, and combinations thereof.

8. The assembly of claim 1, wherein the polymeric washer includes nanoparticles selected from $Al_2O_3$, BaO, CaO, $CeO_2$, MgO, $ZrO_2$, $SiO_2$, $TiO_2$, $Al_2SiO_{53}$, $BaTiO_3$, $SrTiO_2$, zirconia toughened alumina (ZTA), alumina toughened zirconia (ATZ), yttrium stabilized zirconia (YSZ), yttrium-toughened zirconia (YTZP), aluminum nitride (AN), silicon nitride (Si₃N₄), boron nitride (BN), carbon nitride (CN), and combinations thereof.

9. The assembly of claim 8, wherein the nanoparticles range in size from greater than about 100 nanometers (0.1 microns) to about 40,000 nanometers (40 microns).

10. The assembly of claim 8, wherein a nanoparticle loading in the polymeric washer ranges from >0 to about 40%, by weight.

11. The assembly of claim 1, wherein the polymeric washer comprises opposed major side and an adhesive is coated on at least one of the major sides.

12. The assembly of claim 1, wherein the electrical connection material resides in the circuit board third ground via hole connected to a ground metallization connected to the circuit board ground plate and connected to the system ground, the system ground comprising at least one of:
   a) a ground pin welded or brazed to the ferrule;
   b) the gold braze hermetically sealing the insulator to the ferrule; and
   c) a gold pocket pad in the ferrule.

13. The assembly of claim 1, wherein the electrical connection material connects the circuit board ground edge termination to the system ground, the system ground comprising at least one of:
   a) a gold braze hermetically sealing the insulator to the ferrule;
   b) an oxide-resistant metal addition secured to the ferrule; and
   c) a gold pocket pad in the ferrule.

14. An assembly that is attachable to an active medical device (AMD), the assembly comprising:
   a) a metallic ferrule configured to be mounted into an opening of an AMD housing, the ferrule comprising an outer perimeter and an inner perimeter, wherein after installation into the AMD housing, the ferrule has a device side oriented to the inside of the AMD housing and a body fluid side oriented to the outside of the AMD housing;
   b) an insulator hermetically secured to the ferrule in the inner perimeter, the insulator also having an insulator device side and an insulator body fluid side;
   c) a plurality of terminal pins mounted within and extending through a respective one of a plurality of insulator passageways;
   d) a hermetic sealing material between each of the plurality of terminal pins and a respective one of the plurality of insulator passageways;
   e) a circuit board comprising spaced apart circuit board first and second sides, the circuit board supporting at least one circuit board ground plate, wherein the circuit board comprises a plurality of circuit board active via holes conductively isolated from the circuit board ground plate, and wherein the circuit board further comprises a plurality of circuit board ground via holes and either a plurality plus one ground via hole or a circuit board ground termination conductively connected to the circuit board ground plate;
   f) a self-centering polymeric washer positioned between the circuit board first side and the insulator second end surface, the polymeric washer comprising a plurality of non-circular irregularly-shaped openings configured to slip down over each of the plurality of terminal pins with the polymeric washer seated against at least the insulator device side, wherein the non-circular irregularly-shaped openings each have a defined asymmetrical shape to contact each terminal pin in selected clocked positions thereby constraining movement of the self-centering polymeric washer in a planar or x-y direction with respect to the ferrule device side; and
   g) a plurality of filter capacitors supported on the circuit board second side, the plurality of filter capacitors each comprising filter capacitor active and ground terminations, wherein the plurality of filter capacitor active terminations are electrically connected to respective ones of the plurality of terminal pins extending into the plurality of circuit board active via holes, and wherein the plurality of filter capacitor ground terminations are electrically connected to the at least one circuit board ground plate through a respective one of the plurality of circuit board ground via holes; and
   h) an electrical connection material connecting either the circuit board plurality plus one ground via hole or the circuit board edge termination to a system ground.

15. The assembly of claim 14, wherein the first and second filter capacitors are selected from an MLCC chip capacitor and an X2Y attenuator capacitor.

16. An assembly that is attachable to an active medical device (AMD), the assembly comprising:
   a) a feedthrough, comprising:
      i) an electrically conductive ferrule comprising a ferrule sidewall defining a ferrule opening extending to a ferrule body fluid side spaced from a ferrule device side;
      ii) an insulator hermetically sealed to the ferrule in the ferrule opening, the insulator extending to an insulator body fluid side spaced from an insulator device side, wherein, when the ferrule hermetically sealed to the insulator is attached to an opening in a housing of an AMD, the ferrule body fluid side adjacent to the insulator body fluid side, and the ferrule device side adjacent to the insulator device side reside outside and inside the AMD, respectively; and
      iii) at least a first terminal pin hermetically sealed to the insulator in a first via hole by a first braze, wherein the first terminal pin extends outwardly beyond the insulator device side; and
   b) a circuit board comprising spaced apart circuit board first and second sides, the circuit board supporting at least one circuit board ground plate, wherein the circuit board comprises a circuit board first active via hole conductively isolated from the circuit board ground plate, a circuit board first ground via hole conductively connected to the circuit board ground plate, and either a circuit board second ground via hole or a circuit board edge termination conductively connected to the circuit board ground plate;
   c) a polymeric washer positioned between the circuit board first side and the insulator second end surface, the polymeric washer having at least a first opening comprising at least two spaced-apart washer first opening inner arcuate portions that extend inwardly from a washer first opening outer perimeter comprising at least two spaced-apart washer first opening outer perimeter portions, wherein the at least two spaced-apart washer first opening inner arcuate portions are in contact with the first terminal pin so that the polymeric washer is prevented from any lateral movement with respect to the insulator device side, and wherein the at least two spaced-apart washer first opening outer perimeter portions are spaced from the first terminal pin to expose at least two portions of the first braze hermetically sealing the first terminal pin to the insulator in the first via hole;

d) at least a first filter capacitor proximate the circuit board second side, the first filter capacitor comprising a first filter capacitor active and ground terminations, wherein the first filter capacitor active termination is electrically connected to the first terminal pin extending into the circuit board first active via hole, and wherein the first filter capacitor ground termination is electrically connected to the at least one circuit board ground plate through the circuit board first ground via hole; and e) an electrical connection material connecting either the circuit board second ground via hole or the circuit board edge termination to a system ground.

17. The assembly of claim 16, wherein the washer first opening comprises four spaced-apart washer first opening inner arcuate portions that extend inwardly from the washer first opening outer perimeter comprising at least four spaced-apart washer first opening outer perimeter portions, wherein the at least four spaced-apart washer first opening inner arcuate portions are in contact with the first terminal pin so that the polymeric washer is prevented from lateral movement with respect to the insulator device side, and wherein the at least four spaced-apart washer first opening outer perimeter portions are spaced from the first terminal pin to expose at least four portions of the first braze hermetically sealing the first terminal pin to the insulator in the first via hole.

18. The assembly of claim 16, further comprising:
a) at least a second terminal pin hermetically sealed to the insulator in a second via hole by a second braze, wherein the second terminal pin extends outwardly beyond the insulator device side;
b) the polymeric washer having a second opening comprising at least two spaced-apart washer second opening inner arcuate portions that extend inwardly from a washer second opening outer perimeter comprising at least two spaced-apart washer second opening outer perimeter portions, wherein the at least two spaced-apart washer second opening inner arcuate portions are in contact with the second terminal pin, and wherein the at least two spaced-apart washer second opening outer perimeter portions are spaced from the second terminal pin to expose at least two portions of the second braze hermetically sealing the second terminal pin to the insulator in the second via hole;
c) the circuit board further comprising a circuit board second active via hole conductively isolated from the circuit board ground plate and a circuit board third ground via hole conductively connected to the circuit board ground plate, and wherein the first and second terminal pins extend through the washer first and second openings and into the circuit board first and second active via holes; and
d) a second filter capacitor proximate the circuit board second side, the second filter capacitor comprising second filter capacitor active and ground terminations, wherein the second filter capacitor active termination is electrically connected to the second terminal pin extending into the circuit board second active via hole, and wherein the second filter capacitor ground termination is electrically connected to the at least one circuit board ground plate through the circuit board second ground via hole.

19. The assembly of claim 18, wherein at least one of the at least two spaced-apart washer first opening inner arcuate portions and the at least two spaced-apart washer second opening inner arcuate portions are diametrically opposed to each other.

20. An assembly that is attachable to an active medical device (AMD), the assembly comprising:
a) a feedthrough, comprising:
i) an electrically conductive ferrule comprising a ferrule sidewall defining a ferrule opening extending to a ferrule body fluid side spaced from a ferrule device side;
ii) an insulator hermetically sealed to the ferrule in the ferrule opening by a gold braze, the insulator extending to an insulator body fluid side spaced from an insulator device side, wherein, when the ferrule hermetically sealed to the insulator is attached to an opening in a housing of an AMD, the ferrule body fluid side adjacent to the insulator body fluid side, and the ferrule device side adjacent to the insulator device side reside outside and inside the AMD, respectively; and
iii) a first terminal pin hermetically sealed to the insulator in a first via hole by a first terminal pin braze, and a second terminal pin hermetically sealed to the insulator in a second via hole by a second terminal pin braze, wherein the first and second terminal pins extend outwardly beyond the insulator device side; and
b) a circuit board comprising spaced apart circuit board first and second sides, the circuit board supporting at least one circuit board ground plate, wherein the circuit board comprises circuit board first and second active via holes conductively isolated from the circuit board ground plate, and wherein the circuit board further comprises a circuit board first ground via hole and either a circuit board second ground via hole or a circuit board ground termination conductively connected to the circuit board ground plate;
c) a polymeric washer positioned between the circuit board first side and the insulator second end surface, the polymeric washer comprising at least a washer first opening and a washer second opening with the first and second terminal pins extending through the washer first and second openings and into the circuit board first and second active via holes;
d) at least a first filter capacitor proximate the circuit board second side, the first filter capacitor comprising a first filter capacitor first and second active terminations connected to first and second active electrode plates and a first filter capacitor ground termination connected to a ground electrode plate, wherein the first filter capacitor first and second active terminations are electrically connected to the respective first and second terminal pins extending through the washer first and second openings and into the circuit board first and second active via holes, and wherein the first filter capacitor ground termination is electrically connected to the at least one circuit board ground plate through the circuit board first ground via hole; and
e) an electrical connection material connecting either the circuit board second ground via hole or the circuit board edge termination to a system ground.

21. The assembly of claim 20, wherein:
a) the washer first opening comprises a washer first opening inner arcuate portion that contacts the first terminal pin and a washer first opening outer perimeter portion that is spaced from the first terminal pin and that exposes a portion of the first terminal pin braze hermetically sealing the first terminal pin to the insulator in the first via hole; and b) the washer second opening comprises a washer second opening inner arcuate portion that contacts the second terminal pin and a washer second opening outer perimeter portion that is spaced from the second terminal pin and that exposes a portion of the second terminal pin braze hermetically sealing the second terminal pin to the insulator in the second via hole, c) wherein, in an imaginary configuration having the washer first and second openings superimposed one on top of the other and when measured with respect to their orientations in the polymeric washer, the cumulative arcuate distance of the respective washer first and second opening inner arcuate portions about one of the first and second terminal pins, subtracting overlap, results in a gap between the superimposed washer first and second opening inner arcuate portions that is less than a diameter of either of the first and second terminal pins so that the polymeric washer is prevented from lateral movement with respect to the insulator device side.

* * * * *